United States Patent
Itabashi et al.

(10) Patent No.: US 11,130,985 B2
(45) Date of Patent: Sep. 28, 2021

(54) SPOT ARRAY SUBSTRATE, METHOD FOR PRODUCING SAME, AND NUCLEIC ACID POLYMER ANALYSIS METHOD AND DEVICE

(71) Applicant: HITACHI HIGH-TECHNOLOGIES CORPORATION, Tokyo (JP)

(72) Inventors: Naoshi Itabashi, Tokyo (JP); Sonoko Migitaka, Tokyo (JP); Masatoshi Narahara, Tokyo (JP); Tomohiro Shoji, Tokyo (JP); Yukio Ono, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 0 days.

(21) Appl. No.: 15/529,122

(22) PCT Filed: Oct. 7, 2015

(86) PCT No.: PCT/JP2015/078479
§ 371 (c)(1),
(2) Date: May 24, 2017

(87) PCT Pub. No.: WO2016/084489
PCT Pub. Date: Jun. 2, 2016

(65) Prior Publication Data
US 2017/0260573 A1 Sep. 14, 2017

(30) Foreign Application Priority Data
Nov. 27, 2014 (JP) .............................. JP2014-240434

(51) Int. Cl.
*C12Q 1/68* (2018.01)
*C12Q 1/6809* (2018.01)
(Continued)

(52) U.S. Cl.
CPC ........ *C12Q 1/6809* (2013.01); *B01J 19/0046* (2013.01); *C12Q 1/6806* (2013.01);
(Continued)

(58) Field of Classification Search
CPC ............ C12Q 2563/159; C12Q 1/6874; C12Q 1/6809; C12Q 1/6806; B01J 2219/00484;
(Continued)

(56) References Cited

U.S. PATENT DOCUMENTS 6,429,027 B1 * 8/2002 Chee ................ G01N 33/54393
436/518
2002/0172980 A1 * 11/2002 Phan .................... C12Q 1/6816
435/7.1
(Continued)

FOREIGN PATENT DOCUMENTS

JP 2004-500867 A 1/2004
JP 2008-528040 A 7/2008
(Continued)

OTHER PUBLICATIONS

International Search Report of PCT/JP2015/078479 dated Dec. 28, 2015.
(Continued)

*Primary Examiner* — Betty J Forman
(74) *Attorney, Agent, or Firm* — Mattingly & Malur, PC

(57) ABSTRACT

In order to reduce the cost of producing a spot array substrate and reduce the cost of nucleic acid polymer analysis, a spot array substrate is used which is produced by preparing a resin substrate 402 having a surface on which an uneven pattern is formed and a plurality of bead sitting positions set in a two-dimensional array within the uneven pattern, and loading surface-modified beads onto the bead sitting positions of the resin substrate.

9 Claims, 12 Drawing Sheets

(51) Int. Cl.
| | |
|---|---|
| *B01J 19/00* | (2006.01) |
| *C12Q 1/6806* | (2018.01) |
| *C12Q 1/6874* | (2018.01) |
| *G01N 35/00* | (2006.01) |
| *G01N 35/10* | (2006.01) |
| *B32B 27/32* | (2006.01) |
| *C08G 77/50* | (2006.01) |

(52) U.S. Cl.
CPC ... *C12Q 1/6874* (2013.01); *B01J 2219/00421* (2013.01); *B01J 2219/00466* (2013.01); *B01J 2219/00621* (2013.01); *B01J 2219/00648* (2013.01); *B01J 2219/00659* (2013.01); *B01J 2219/00722* (2013.01); *B32B 27/32* (2013.01); *C08G 77/50* (2013.01); *G01N 2035/00237* (2013.01); *G01N 2035/1034* (2013.01)

(58) Field of Classification Search
CPC .... B01J 2219/00421; B01J 2219/00621; B01J 2219/00648; B01J 2219/00659; B01J 2219/00317; B01J 2219/005; B01L 2200/0642; B01L 2200/0668; B32B 27/32; G01N 15/10; G01N 2001/282; G01N 2001/2833; G01N 33/54306; G01N 3/54313
See application file for complete search history.

(56) References Cited

U.S. PATENT DOCUMENTS

| | | | |
|---|---|---|---|
| 2003/0003496 A1 | 1/2003 | Bradley et al. | |
| 2003/0006143 A1* | 1/2003 | Banerjee | G03F 7/164 205/414 |
| 2005/0074787 A1 | 4/2005 | Fan et al. | |
| 2007/0099222 A1 | 5/2007 | Gee et al. | |
| 2008/0206101 A1* | 8/2008 | Huang | B01L 3/5027 422/68.1 |
| 2011/0136677 A1* | 6/2011 | Oldham | G01N 35/00069 506/6 |
| 2012/0316087 A1* | 12/2012 | Sugimura | B01L 3/502715 506/38 |
| 2013/0102500 A1* | 4/2013 | Stumber | B01J 19/0046 506/13 |
| 2014/0323330 A1* | 10/2014 | Bergo | G01N 33/54373 506/9 |

FOREIGN PATENT DOCUMENTS

| | | |
|---|---|---|
| JP | 2009-060859 A | 3/2009 |
| JP | 2009-513137 A | 4/2009 |
| JP | 2009-537126 A | 10/2009 |
| JP | 2010-008391 A | 1/2010 |
| JP | 2010-513869 A | 4/2010 |
| JP | 2011-153938 A | 8/2011 |
| JP | 2013-150567 A | 8/2013 |
| WO | 2006/084132 A2 | 8/2006 |
| WO | 2007/132002 A1 | 11/2007 |
| WO | 2008/076406 A2 | 6/2008 |
| WO | 2011/026102 A1 | 3/2011 |

OTHER PUBLICATIONS

Chinese Office Action received in corresponding Chinese Application No. 201580064597.9 dated Sep. 10, 2019.
Japanese Office Action received in corresponding Japanese Application No. 2018-217491 dated Oct. 23, 2019.
Biyani, M. et al., "Kilo-To-Giga DNA Microarray for Conversion into High-Density Protein Microarray on Demand", TAS 14th International Conference on Miniaturized System for Chemistry and Life Science, 2010, pp. 734-736.

* cited by examiner

FLOW DIRECTION OF LIQUID (a)

(b)

(c)

SPOT ARRAY SUBSTRATE, METHOD FOR PRODUCING SAME, AND NUCLEIC ACID POLYMER ANALYSIS METHOD AND DEVICE

TECHNICAL FIELD

The present invention relates to the analysis of a biomolecule, specifically, a spot array substrate for decoding the base sequence of a nucleic acid polymer at high efficiency and high accuracy, a method for producing the same, and a nucleic acid polymer analysis system using the spot array substrate.

BACKGROUND ART

Patent Literature 1 describes a method for using a DNA chip to detect the expression of conventionally known genes, and describes that a transparent resin (polycarbonate, polypropylene and cycloolefin-based polymer) having little self-fluorescence is used to detect fluorescent light indicating the presence of a gene. Patent Literature 1 describes that a plurality of concave portions are formed (arrayed) on the substrate surface as the array spot, that the substrate's bottom surface is desirably flat, and that the detection of the target DNA can be performed by immobilizing an oligo DNA on the inner surface of the concave portion, immobilizing a conventionally known probe DNA in advance on the bottom surface of a concave portion, and adding a solution filled with the sample which is the object for analysis.

Patent Literature 2 describes a method for using a microarray to detect the expression of conventionally known genes, and describes that a transparent resin (cycloolefin-based polymer) having little self-fluorescence is used to detect fluorescence indicating the presence of a gene. Patent Literature 2 describes the method for immobilizing an oligo DNA on a substrate as a well-known method in the field, and describes that the presence or absence of expression can be determined by hybridizing with the target DNA on a substrate on which a conventionally known probe DNA is immobilized on an array spot in advance.

Patent Literature 3 describes a method for using a microarray to detect the expression of conventionally known genes, and describes that a functional group can be used in order to immobilize an oligo DNA on a substrate and that a polymer having chemical and thermal stability, low fluorescence and optical stability, preferably a cycloolefin polymer, and preferably Zeonex® or Zeonor® is used in the substrate.

Patent Literature 4 describes a method for using a microarray to detect the expression of a conventionally known gene, and describes hybridization with the target DNA on a substrate on which a conventionally known probe DNA is immobilized on the array spot in advance, and use of a substrate including a multi-well (namely, the concave portion of the array) cycloolefin polymer when performing fluorescence detection with the substrate.

Patent Literature 5 describes a method for using an Si substrate which forms a highly integrated array of the concave portion having an electrode on the bottom surface by a semiconductor process to analyze a nucleic acid polymer. Patent Literature 5 describes that the base sequence can be decoded by loading the beads which form the replicas of the template DNAs derived from the object for analysis on the surface in advance in the concave portion which is formed as an array on the substrate surface, and detecting the ions emitted from the replica of these template DNAs due to the reaction with a reagent with an electrode provided on the bottom surface of the concave portion.

CITATION LIST

Patent Literature

Patent Literature 1: JP 2009-60859 A
Patent Literature 2: JP 2009-513137 A (US 2007/0099222 A1)
Patent Literature 3: JP 2009-537126 A
Patent Literature 4: JP 2004-500867 (US 2003/0003496 A1)
Patent Literature 5: JP 2010-513869 A

SUMMARY OF INVENTION

Technical Problem

Various methods such as a method for optically measuring and discriminating bases and a method for electrically measuring and discriminating bases have been examined as methods for analyzing nucleic acid polymers such as DNA and RNA. As one method, a fluorescence system DNA sequencer decodes the bases by analyzing the fluorescence generated when reacting a reagent including a fluorescent dye and an enzyme with a DNA. It is anticipated that studying and elucidating the causal relationship between nucleotide sequence information and pathology revealed by such nucleic acid polymer analysis techniques will expand the applications to medical diagnosis. However, presently, methods are mostly used in research applications and the cost of one analysis is also high. It is furthermore desirable to greatly reduce the analysis cost in order for the method to spread widely as a medical diagnostic technology in the near future. Meanwhile, improvements for obtaining a large amount of data from a small number of samples in a high throughput, and improvements for reducing (cost reduction including consumable parts for analysis, reagents, etc.) the analysis cost necessary to obtain the same amount of data are continuously pursued.

It is necessary to improve the data acquisition efficiency in order to increase the reduction of the amount of the sample, the miniaturization of the analysis cell, and the volume of data acquired. Conventionally, a fluorescence system DNA sequencer measures the fluorescence generated by the reaction in a state in which the object for analysis is randomly scattered in a plane, and practical application has started in the form which discriminates the bases from the data analysis of a fluorescence bright spot of random positions. However, because the analysis was random, the region in which the object for analysis might not be present and the region in which the analysis was not possible due to the overlapping and mixing of the fluorescence from an adjacent object for analysis existed, and the usage efficiency in the region on the substrate of a flow cell where the reaction event occurs was low. As a result, the sample which was the object for analysis which did not contribute to the analysis was generated, and the area of the flow cell for analysis had to be expanded in order to separate from the events of a nearby region to obtain a sufficient amount of data.

An integrated array has been considered as a promising method for solving this problem. It is one general concept for highly efficiently executing the task in the smallest area possible. It is possible to eliminate interference with an adjacent fluorescence event and maximize the volume of data acquired per unit substrate area by maintaining the spot in which the object for analysis can be immobilized on the substrate of the flow cell at a pitch which is a specific interval or more from an adjacent spot and arranging discretely and as closely as possible.

However, in order to form a highly integrated spot array on the substrate of the flow cell, it is necessary to use some fine patterning technology such as a semiconductor process like lithography and dry etching micro-machining or drawing and machining by a beam in the production of the substrate. Needless to say, if the semiconductor process which can form various patterns on an Si wafer is used, it is possible to mass-produce the substrate on which a highly integrated spot array is formed, but a considerable increase of the cost of producing the substrate is inevitable compared to flat substrates which have been used in conventional analysis of random fluorescence. A production technique which will greatly reduce the substrate material cost and the cost of producing the spot array is desired.

This technique is different from a DNA sequencer for decoding an unknown base sequence, but a DNA chip (microarray) may be provided as the technology for determining the presence or absence of a conventionally known base sequence. However, this is limited to the application for determining the presence or absence of the same alignment as a conventionally known probe DNA, thus, the number of array spots placed on the chip is different from the situation in which the DNA sequence for which throughput is sought by requiring nothing more than the number of objects for analysis and acquiring as much data as possible by increasing in parallel the degree of integration of the array as much as possible. Therefore, presently, the degree of integration of DNA chips is not so high, and many are measured with an array spot having large dimensions of up to a level of several 100 to several 10 µm. The spot region is arranged in an array for examining the target DNA which is the object for analysis, and the respective spot regions are subjected to functional group modification, the immobilization of the oligo DNA, the immobilization of the probe DNA, etc. However, since the dimensions are large, the spot region can be produced without patterning at the micronization level (several µm to several 100 nm level) which uses a high cost semiconductor process. Further, if the self-fluorescence of the substrate material that interferes with the fluorescence measurement is sufficiently low, there are few other restrictions regarding changing the substrate material. Therefore, cost reductions such as the application of a resin substrate have been made for DNA chips. Patent Literatures 1 to 4 disclose the formation of DNA chips which use a resin substrate having low self-fluorescence in the DNA chip to form functional groups and a spot such as oligo DNA in an array shape on the surface.

Meanwhile, in a DNA sequencer, it will be necessary in the future to continuously acquire unknown sequence data in large quantities and at high throughput, thus, even higher integration is necessary. Therefore, it is necessary to form a spot array at a dimension level of several micrometers to several µm to several 100 nm which is at least one order of magnitude higher than the chip. Presently, the high integration (pitch) of the spot array has a limit due to constraints such as the pitch of the pixels of the photodetector array which detects the fluorescence from the array spot, and thus, the integration remains at the current range of micronization, but it is necessary to acquire unknown sequence data in large quantities and at high throughput, thus, even higher integration will be sought in the future. However, when using a semiconductor process to form a highly integrated array spot at a dimension level of several µm to several 100 nm, a high cost is involved in the production process, thus, for example, the reduction of the total cost of production is insufficient even if a resin substrate is used in order to keep the material cost low. Even though the resin substrate material itself is equivalent to or higher than a material such as quartz and Si in terms of coat and optical performance (low self-fluorescence, etc.), in a DNA sequencer which must improve the data acquisition efficiency by further micronization and higher integration, if a production cost is required in the formation of a highly integrated array, for example, the reduction effect of the final analysis cost will be diminished even if the data acquisition efficiency improves due to higher integration.

However, the application of a highly integrated array has been spreading not only in the analysis of nucleic acid polymers by optical measurement but also in the analysis by electric measurement. Patent Literature 5 discloses the formation of an Si substrate on which a highly integrated array is formed by the semiconductor process in the concave portion having an electrode on the bottom surface, and a method for loading the beads which formed the replica of the template DNA derived from the object for analysis on the surface in advance in each concave portion of the Si substrate surface and electrically measuring and decoding the base sequence. However, in this method, it is necessary to provide a fine electrode for detecting the signals in the concave portion, wiring for connecting thereto, and switches in the substrate to be used, and thus, the substrate is more complicated than the one used in optical measurements. Therefore, the production using the resin substrate having a low material cost is not easy, and all of the substrates must be produced in a high cost semiconductor process.

As stated above, in a DNA sequencer which requires further micronization and higher integration, even with a low cost substrate material, or, even with either optical measurement or electric measurement, as long as a semiconductor process such as lithography or dry etching micromachining is used to produce all of the highly integrated array substrates, there is a limit to the reduction of the cost of production. It is desired to establish a large-scale production technique without using the semiconductor process in the production of all of the substrates.

Solution to Problem

The spot array substrate according to the present invention includes a resin substrate having a surface on which an uneven pattern is formed, a plurality of bead sitting positions set in a two-dimensional array within the uneven pattern, and surface-modified beads loaded onto the bead sitting positions of the resin substrate.

As an example, the uneven pattern is a pattern in which the adjacent bead sitting positions are connected with a groove having a width narrower than the dimension of the bead sitting positions.

The surface-modified beads are immobilized onto the bead seating positions of the resin substrate by physical fitting or a chemical bond or both.

The surface-modified beads may be the functional group surface-modified beads or oligo DNA surface-modified beads. Further, the surface-modified beads may be the beads which form in advance the replica of the template DNA derived from the object for analysis on the oligo DNA surface-modified beads.

The surface density of the bead sitting positions, as an example, is preferably $6.6 \times 10^6/cm^2$ to $180 \times 10^6/cm^2$.

The production method of the spot array substrate according to the present invention includes a step of preparing a resin substrate having a surface on which an uneven pattern is formed and a plurality of bead sitting positions set in a two-dimensional array within the uneven pattern, and a step of loading the surface-modified beads onto the bead sitting positions of the resin substrate.

A centrifugal force or a magnetic force can be used in the step of loading the surface-modified beads onto the bead sitting positions of the resin substrate.

A spot array substrate production kit of the present invention is provided with the resin substrate having a surface on which an uneven pattern is formed, a plurality of bead sitting positions set in a two-dimensional array within the uneven pattern, and surface-modified beads loaded onto the bead sitting positions of the resin substrate. The spot array substrate can be prepared by loading the surface-modified beads such as the functional group surface-modified beads or the oligo DNA surface-modified beads onto the bead sitting positions of the resin substrate. Further, if the beads which form the replica of the template DNA derived from the object for analysis in advance on the beads subjected to surface modification such as the oligo DNA are used as the surface-modified beads, for example, the user of the nucleic acid polymer analysis device can prepare the spot array substrate by loading these beads onto the bead sitting positions after forming the replica of the template DNA on the surface of the oligo DNA surface-modified beads included in the kit by a method such as emulsion PCR.

The nucleic acid polymer analysis device of the present invention is provided with a flow cell in which the aforementioned spot array substrate is incorporated, a reagent supply unit for selectively supplying to the flow cell a plurality of reagents including a reaction reagent including fluorescent dyes which can discriminate the bases of a DNA molecule, a reaction reagent which can cut a dye from dNTP, and a washing reagent for washing inside the flow cell, a temperature control unit for controlling the temperature of the flow cell, a light source for illuminating the excitation light on the spot array substrate, a photodetector array for measuring the fluorescence generated from each bead sitting position of the spot array substrate, and an analyzing device for analyzing a detection signal from the photodetector array.

The analysis method of the nucleic acid polymer according to the present invention includes, as an example, a first step of immobilizing template DNA beads prepared by replicating, on a surface in advance, template DNA derived from a sample which is the object for analysis on the functional group surface-modified beads of the aforementioned spot array substrate, a second step in which the reagent including the fluorescent dye performs an elongation reaction of one base of the template DNA on the template DNA beads immobilized on the functional group surface-modified beads, a third step of measuring optical signals generated from the bead sitting positions of the spot array substrate by illuminating excitation light after the reaction, a fourth step of cleaving the fluorescent dye from the bases in which the optical signals are measured, a fifth step of washing the solution including the cleaved fluorescent dye, and a sixth step of analyzing the optical signals obtained by the third step to determine the base sequence of the template DNA.

The analysis method of the nucleic acid polymer according to the present invention includes, as an example, a first step of loading template DNA beads prepared by replicating, on a surface in advance, the template DNA derived from a sample which is the object for analysis in the bead sitting positions of the resin substrate having the aforementioned surface on which an uneven pattern is formed, and a plurality of bead sitting positions set in a two-dimensional array within the uneven pattern, a second step in which the reagent including the fluorescent dye performs an elongation reaction of one base of the template DNA on the template DNA beads loaded onto the bead sitting positions, a third step of measuring the optical signals generated from the bead sitting positions of the spot array substrate by illuminating the excitation light after the reaction, a fourth step of cleaving the fluorescent dye from the bases in which the optical signals are measured, a fifth step of washing the solution including the cleaved fluorescent dye, and a sixth step of analyzing the optical signals obtained in the third step to determine the base sequence of the template DNA.

The analysis method of the nucleic acid polymer according to the present invention includes, as an example, a first step of immobilizing the template DNA derived from a sample which is the object for analysis on the oligo DNA surface-modified beads of the aforementioned spot array substrate, a second step of replicating the template DNA immobilized on the oligo DNA surface-modified beads, a third step in which the reagent including the fluorescent dye performs an elongation reaction of one base of the template DNA on the oligo DNA surface-modified beads, a fourth step of measuring the optical signals generated from the bead sitting positions of the spot array substrate by illuminating the excitation light after the reaction, a fifth step of cleaving the fluorescent dye from the bases in which the optical signals are measured, a sixth step of washing the solution including the cleaved fluorescent dye, and a seventh step of analyzing the optical signals obtained in the fourth step to determine the base sequence of the template DNA.

Advantageous Effects of Invention

According to the present invention, a fine structure formation at a dimension level of several μm to several 100 nm is possible, and, the spot array substrate (or a kit for preparing the spot array substrate) made by patterning the material (functional group spot, oligo DNA spot, etc.) of the array spot to an array shape can be mass-produced at a low cost. Further, nucleic acid polymer analysis at a low consumables cost can be realized by using a substrate (or, a kit for preparing a substrate) produced in this manner.

Other problems, configurations, and effects will become apparent from the following description of embodiments.

DESCRIPTION OF EMBODIMENTS

Figure 2:
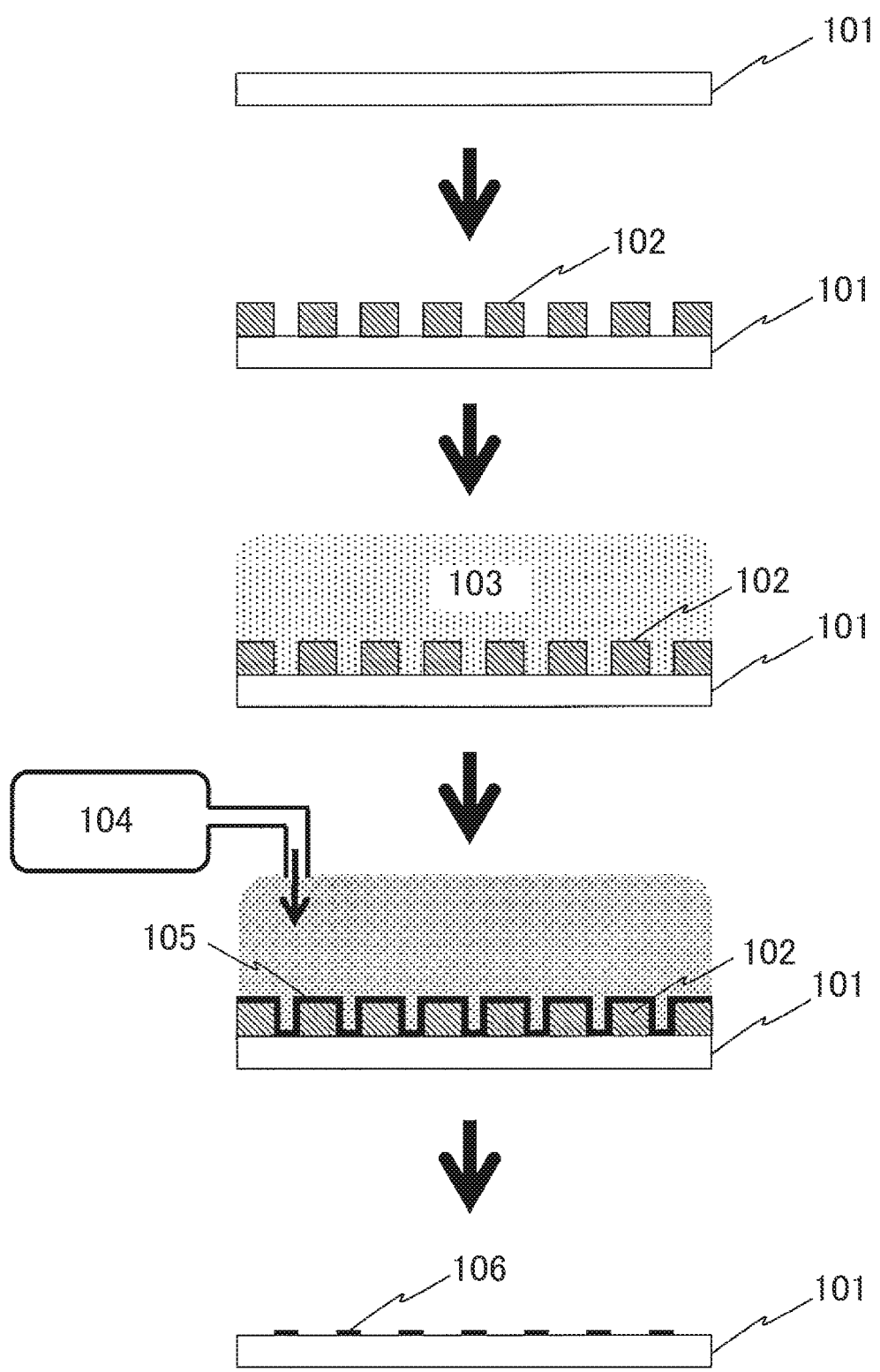
FIG. 2 is a diagram for explaining an example of the production flow for forming the spot array on an Si substrate by a semiconductor production process.

For the purpose of summarizing the conventional array substrate production technique, FIG. 2 illustrates an example of the production step of forming a spot array on an Si substrate by a semiconductor production process. For example, when forming an amino group spot as the functional group spot, a resist pattern 102 is formed by photolithography on an Si wafer 101, its opening (for example, when viewed from above, an opening such as a circle or a square) is subjected to a slight oxidation treatment with oxygen plasma 103, then, an aminosilane film 105 is vapor deposited by an aminosilane-based gas 104, and the substrate on which an amino group spot array is formed can finally be produced by a flow which removes the resist pattern 102 by wet washing. Alternatively, after first forming the aminosilane film on the Si wafer, and forming a spot pattern mask (for example, when viewed from above, a mask such as a circle or a square) by photolithography, the amino group spot array can be produced by removing the aminosilane film of a planar region other than the spot by dry etching and then peeling the resist mask.

However, in such a production method, it was necessary to use an Si substrate for the semiconductor process in the respective substrate materials, and it was necessary to subject all of the wafers to a treatment by a semiconductor process such as lithography, plasma treatment or dry etching, or vapor deposition. Thus, the reduction of the cost of production was limited. Further, other than the production step illustrated above, there are methods which can form the spot array such as processing by an ion beam and electric beam film deposition, but such a beam drawing production method becomes more costly as the number of spots increases. Thus, it cannot become a low cost mass production method compared to wafer batch processing.

The embodiments of the present invention will be explained in detail below based on the drawings. The configuration and the materials described in the embodiments serve to solely illustrate implementations of the spirit of the present invention, and are not intended to strictly specify materials, dimensions, and other such variables in any way.

First Embodiment

A first embodiment describes a production example of the spot array substrate which uses a resin substrate to form a functional group spot array or an oligo DNA spot array.

Figure 1:
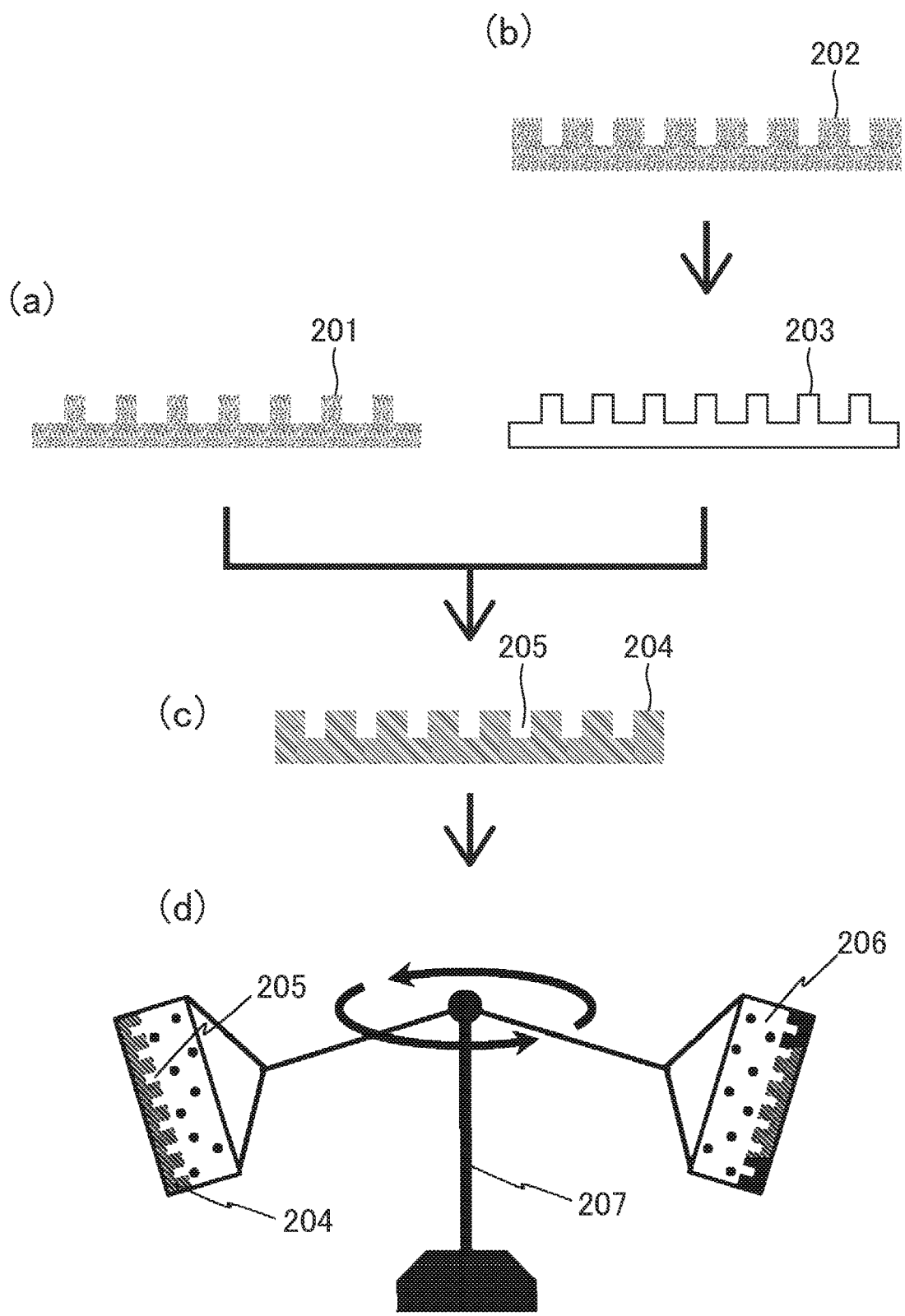
FIG. 1 is an explanatory drawing illustrating an example of the production step of forming the spot array on the resin substrate.

FIG. 1 is an explanatory drawing illustrating the basic production process of the present embodiment which forms the spot array on the resin substrate. To summarize, this is a method for producing a spot array substrate at a low cost by preparing the resin substrate on which the uneven pattern is formed on the surface and in which a plurality of bead sitting positions are set in a two-dimensional array within the uneven pattern, and loading the surface-modified beads such as the functional group surface-modified beads or the oligo DNA surface-modified beads onto the bead sitting positions of the resin substrate. The bead sitting position is a space in which a portion or the whole of the region is surrounded by the convex portion of the uneven pattern, and having dimensions in which the beads fit snugly.

FIG. 1(a) illustrates a method for directly using an Si mold. In this method, the Si wafer is processed by a semiconductor process (lithography, dry etching, and asking) to produce an Si convex minute mold (master) 201. FIG. 1(b) illustrates a method for using Ni electroforming. This method prepares a sub master by the Ni electroforming, and transfers the Si concave minute mold (master) 202 after production to the Ni convex mold (sub master) 203. First, at least one of convex molds 201 and 203 is prepared by any of the methods. Then, as shown in FIG. 1(c), the mold is used to produce the resin substrate 204 on which the array 205 of the concave portion is formed. It is possible in this formation step to mass-produce the resin substrate 204 from the resin raw material by injection molding. Further, the resin substrate 204 can be mass-produced by thermal deformation (thermal imprint) of a resin plate (or, if thin, a resin film) prepared in advance as a plate-like or sheet-like material.

In the present embodiment, as an example, the Ni convex mold (sub master) 203 shown in FIG. 1(b) was used, a cycloolefin-based polymer such as a cycloolefin polymer (COP) or a cycloolefin copolymer (COC) was used as an example of the resin material, and 1000 molded articles were prepared by injection molding, and as a result, the articles could be prepared without problems. Lastly, the spot array was formed. In this step, as shown in FIG. 1(d), the resin substrate 204 on which the array 205 of the concave portion was formed was placed in a centrifuge 207 in order to generate a centrifugal force in the direction in which the beads enter the concave portion in a state in which, as an example, the resin substrate 204 was immersed in a liquid 206 with the silica amino group surface-modified beads (diameter: 1 μm) dispersed in it, and rotated at 3000 rpm for 10 minutes. The spherical beads used had a variation in the particle diameter of CV10%.

Whether or not the beads entered the bead sitting positions formed by the concave portion was checked by an electron microscope, and the amino modified beads were loaded in 40% of all of the concave portions, but the beads were not loaded in 60% of the concave portions. In order to estimate the cause thereof, the substrate was carefully observed with an optical microscope in a state in which it was immersed in the liquid in which the beads were dispersed, and as a result, a situation was observed in which a variety of large and small air bubbles remained. It can be seen that the air bubbles interfere with the loading of the beads. Therefore, it was assumed that the fact that the air bubbles were likely to remain and the liquid was unlikely to enter the concave portion formed by the convex mold was the cause that made it difficult to fit the beads, and the two air bubble reduction measures of the change in the layout of the mold and the liquid replacement from the alcohol to the aqueous solution were implemented as measures against the above.

Figure 3:
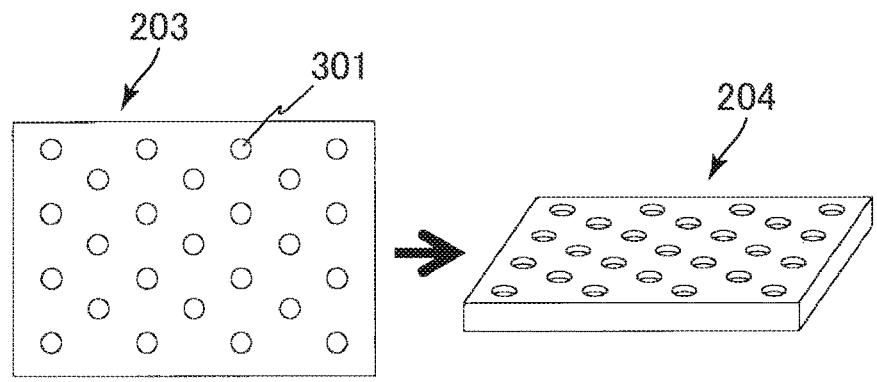
FIG. 3 is a top view of a Ni concave mold and a schematic diagram of the resin substrate produced using the mold.

FIG. 3 shows a top view of the Ni convex mold 203 used in the above-described test production and shows a schematic diagram of the resin substrate 204 produced using the mold. The convex portion 301 of the mold is transferred to the resin to form the concave portion in the resin substrate 204. With respect to the spherical beads having a diameter of 1 μm, the cylindrical concave portion had a diameter of 1 μm and the density of the concave portion was $6.6 \times 10^6/cm^2$ (4.2-μm pitch). Note that, the abbreviated expression "1-μm spherical beads are loaded in the cylindrical concave portion having a diameter of 1 μm" simply describes an example of the dimensions. Actually, it is desirable, for example, to make the concave portion to some normal taper (for example, only +5° from the vertical is set as an example of the normal taper in the concave portion in which the depth is 1.1 μm, the diameter of the upper opening of the concave portion is 1.1 μm, and the diameter of the bottom of the concave portion is 0.9 μm), so that it is difficult for the beads to fallout as the beads more easily enter the upper opening thereby, and the beads are fitted after entering the upper opening. However, it goes without saying that it is easier for the beads to enter the upper opening when the diameter of the upper opening of the concave portion is slightly larger than the beads, and properly fitting the bead into a slightly normal taper makes it more difficult for the beads to fall out by properly fitting the beads into a slightly normal taper, and the state in which this kind of detailed design is implemented may be simply expressed as "1-μm spherical beads are loaded in the cylindrical concave portion having a diameter of 1 μm". Further, designs, for example, which consider the variation of the beads and make a slightly more normal taper (for example, making the normal apex to only +10°), and other than this, designs which attach roundness (R) to the upper opening, or which are subjected to chamfering (C) can be easily be conceived of.

Figure 4:
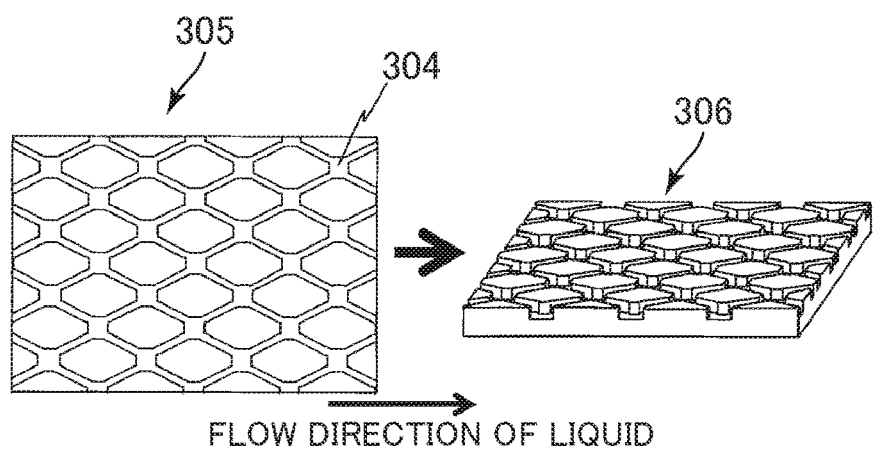
FIG. 4 is a top view of the Ni mold and a schematic diagram of the resin substrate produced using the mold.

FIG. 4 is a top view of an example of the improved Ni mold 305 and is a schematic diagram of the resin substrate 306 produced using the mold. The Ni mold 305 has an uneven pattern in which the portion of the densely arranged rhombuses (to be precise, rhombuses having a chamfered vertex) is hollow and the portion between the adjacent rhombuses protrudes. The resin substrate 306 produced in the mold is made as a measure for improving the filling rate of the beads, and the arrangement of the bead sitting positions is the same as FIG. 3, but a straight flow path is formed in the flow direction of the liquid, and the liquid flows in easily (the air bubbles are unlikely to remain). It is therefore anticipated that the beads are easily fitted. The convex portion 304 of the mold 305 is transferred to the resin and the groove is formed in the resin substrate 306 as the concave portion. In this example, it becomes the layout of an intersecting groove. As an example of the dimensions, the groove has a depth of 1.1 μm, and a width of 0.6 μm, and the width is smaller than the beads' diameter 1 μm. Thus, the beads are not loaded in the groove. The grooves intersect and the intersection point portion is the bead sitting position. The intersection point portion was made to be 1 μm (as stated above, the width of the upper part is actually a dimension which is slightly larger than the intersection point, and, some normal taper) for the dimension of the narrowest portion, and a layout design in which the beads having a diameter of 1 μm could be loaded was made.

The mold shown in FIG. 4 was used to prepare 1000 molded articles by injection molding. Compared to the substrate of FIG. 3, there is a flow path and the shape is somewhat complicated, but as a result of the test production by injection molding, it was found that articles could be produced without any problems as well in FIG. 4.

Therefore, lastly, the resin substrate having the improved layout was immersed in the liquid 206 in which the silica surface amino group modified beads were dispersed as shown in FIG. 1(d). However, in this case, the resin substrate having the improved layout was immersed once in isopropyl alcohol before being immersed in the liquid 206 in which the silica amino group surface-modified beads were dispersed. Then the substrate was replaced with the aqueous solution while it was carefully observed that no air bubbles were produced, and replaced with the liquid 206 in which the surface amino group modified silica beads were dispersed. In this state, in order to load the amino group surface-modified beads in the bead sitting positions set in the intersection point of the groove in a pattern in which the concave portion, namely, the portion between the rhombuses was the groove, the substrate was placed in the centrifuge 207, and rotated at 3000 rpm for 10 minutes. It was checked by an electron microscope as to whether or not the beads entered the bead sitting portions of the intersection point of the groove, and the amino group modified beads entered 80% of all the bead sitting positions, thus, an improvement was seen, but the beads still did not enter 20% of the bead sitting positions.

After running the aqueous solution of the reagent for analysis for 12 hours while repeating the temperature control (10 to 70° C.) for controlling the enzyme reaction in order to simulate the use in the subsequent analysis, the beads which entered the bead sitting positions of the intersection point of the grooves were again verified by an electron microscope. As a result, 10% of the beads fell out, and the filling rate decreased to 70% of the total. While the filling rate of the substrate of the present embodiment was slightly low, it was a production method merely for fitting the array spot material on a low-cost molded resin substrate, thus, it was confirmed that the substrate could be produced at a remarkably low cost, and the method was a superior production method.

As an example, in the present embodiment, the bulk material in which the amino group was modified was used as an example of a functional group on the surface of the silica beads as the material of the array spot. Further, an example for loading the beads in the concave portion of the resin substrate by a centrifuge (or a rotary machine similar thereto) has been described. However, it goes without saying that the present embodiment may also be applied to the surface-modified beads in other functional groups, and, the bulk material of the beads is not limited to silica.

Figure 5:
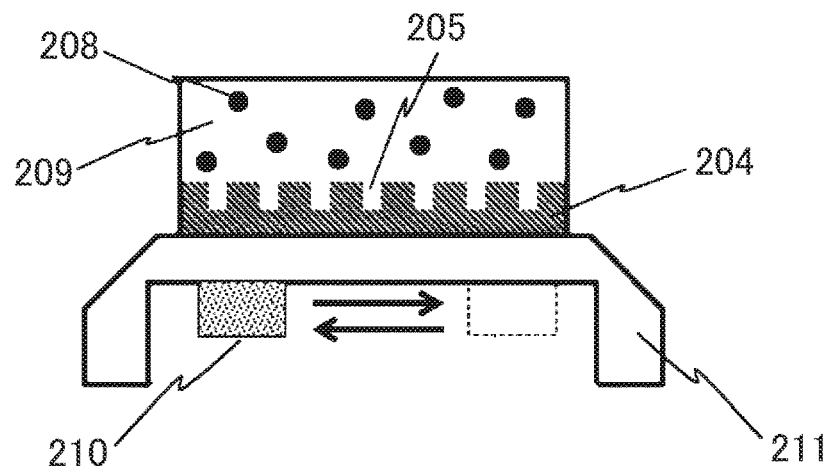
FIG. 5 is an explanatory drawing of an example of using a magnetic force in the spot array formation.

The amino group surface-modified magnetic beads 208 containing a magnetic material can be used as, for example, the bulk material of the beads. In this case, as shown in FIG. 5, the beads can be loaded in the convex portion of the array 205 by setting the resin substrate 204 which forms the concave portion of the array 205 in a container, immersing the solution 209 in which the amino group surface-modified magnetic beads 208 are dispersed, and then using the device 211 which moves the magnet while attracting the magnetic force to the magnetic beads by a magnet 210 from the back surface of the resin substrate. Also in the case of using a device 211 in which the magnet moves while attracting with the magnet 210 from the lower side, the loading rate was higher when loading the beads after sufficiently removing the air bubbles in the same manner as the case of using the centrifuge, and the phenomenon in which some of the beads fall out was observed by a heat cycle test run for 12 hours which repeated the subsequent temperature control (10 to 70° C.). As stated above, even if the bulk material of the beads is changed and the force for loading the beads is changed to a magnetic force from a centrifugal force, the loading of the beads onto the bead sitting positions of the substrate is possible in the same manner.

Further, in the description above, the detailed results such as the loading rate regarding the loading of the beads into the concave portion of the simple spot array layout (bottomed hole) as shown in FIG. 3, and the loading of the beads into the concave portion (intersection position of the groove) of the groove of the layout in which the grooves intersect and the intersection point thereof is dimensioned to be able to load the beads as shown in FIG. 4 have been explained as an example. But the design of the concave portion of the surface is not limited thereto.

Figure 6:
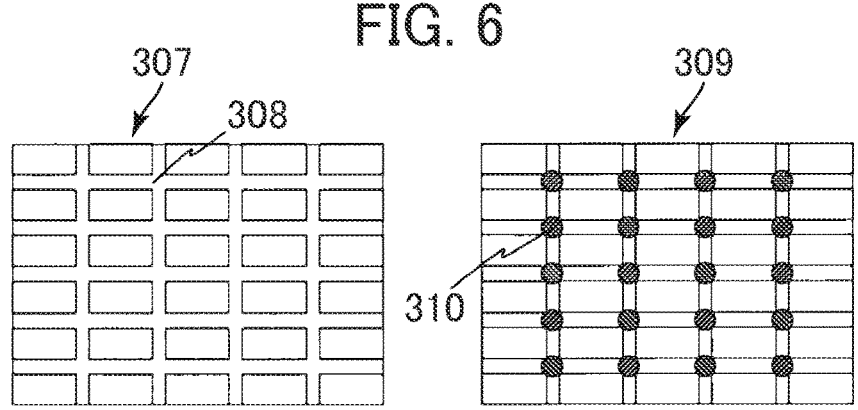
FIG. 6 is a schematic diagram illustrating an example of the uneven pattern provided on the surface of the resin substrate.
Figure 7:
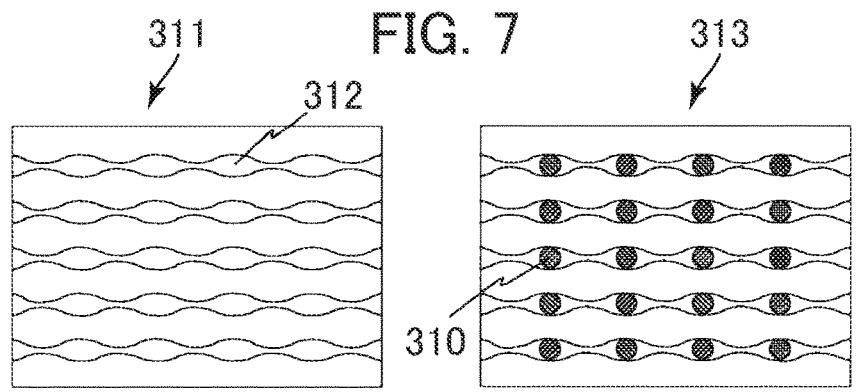
FIG. 7 is a schematic diagram illustrating an example of the uneven pattern provided on the surface of the resin substrate.
Figure 8:
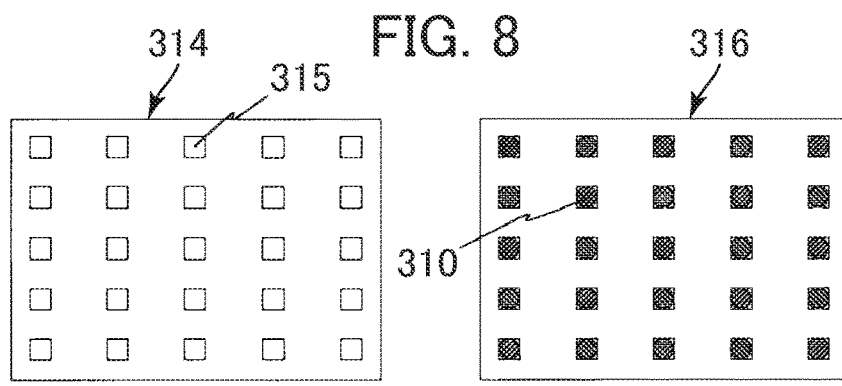
FIG. 8 is a schematic diagram illustrating an example of the uneven pattern provided on the surface of the resin substrate.
Figure 9:
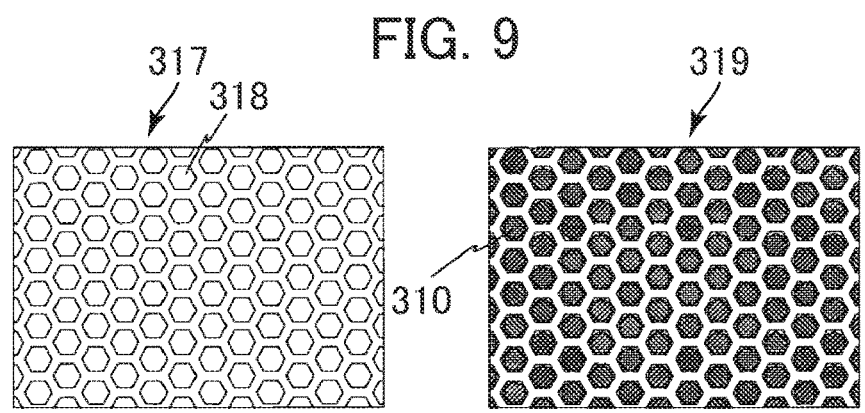
FIG. 9 is a schematic diagram illustrating an example of the uneven pattern provided on the surface of the resin substrate.
Figure 10:
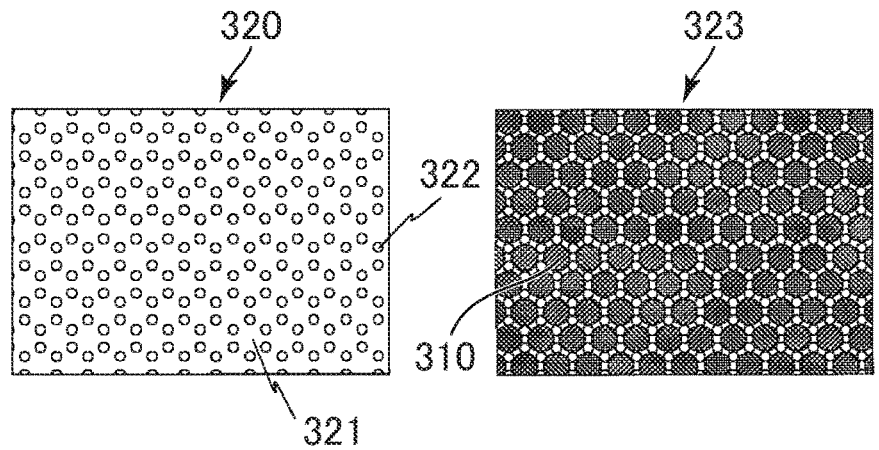
FIG. 10 is a schematic diagram illustrating an example of the uneven pattern provided on the surface of the resin substrate.

FIG. 6 to FIG. 10 are schematic diagrams illustrating other examples of the uneven pattern provided on the surface of the resin substrate. In all of the drawings, the left side of the drawing is the schematic top view of the resin substrate in which the beads are not fitted, and the right side of the drawing is the schematic top view of the spot array substrate produced by fitting the surface-modified beads into the bead sitting positions. The concept common to the uneven patterns formed on the surface of the resin substrate shown in FIG. 6, FIG. 7, and FIG. 10 is the patterns which connect the adjacent bead sitting positions with the groove having a width narrower than the dimension of the bead sitting positions.

FIG. 6 is a schematic diagram illustrating an example of the resin substrate 307 in which a plurality of grooves orthogonal to each other are formed vertically and horizontally on the surface, and the intersection of the vertical groove and the horizontal groove becomes the bead sitting position. The bead sitting positions 308 construct the two-dimensional array and are arranged on the resin substrate 307. The width of the groove is set to be slightly smaller than the diameter of the beads, thus, the beads cannot enter the linear grooves which connect the intersections together. However, the bead sitting positions 308 produced by the intersection of the vertical groove and the horizontal groove have dimensions so that only the beads having a diameter of 1 µm fit. Therefore, the beads can be fitted in the bead sitting positions due to the centrifugal force and the magnetic force. As shown in the figure, the beads having a larger diameter than the width of the groove are fit in the bead sitting positions formed by the intersection of the vertical groove and the horizontal groove of the resin substrate, and as a result, the spot array substrate 309 in which the surface-modified beads 310 are arranged in a two-dimensional array on the surface can be obtained.

FIG. 7 is a schematic diagram illustrating an example of the resin substrate in which a plurality of grooves with constrictions are formed in parallel on the surface. On the surface of the resin substrate 311, a plurality of grooves in which the locations in which the width increases and the locations in which the width decreases are alternately connected are formed in parallel without intersecting with each other. The width of the groove is a dimension which permits the fitting of the beads at the locations in which the width increases. Therefore, the portions having the increased width among the grooves having constrictions become the bead sitting position 312, and a spot array substrate 313 in which the surface-modified beads are arranged in a two-dimensional array on the surface can be obtained by fitting the surface-modified beads 310 in the bead sitting positions. In the case of the resin substrate 311, the grooves do not intersect, but because a liquid easily flows into them, they are easier for the beads to enter than the bead sitting positions formed of at least an isolated circular bottomed hole, and the bead loading rate can be increased.

FIG. 8 is a schematic diagram illustrating an example of the resin substrate in which the bead sitting positions formed of a square bottomed hole are formed in a two-dimensional array on the surface. The resin substrate 314 is similar to the resin substrate shown in FIG. 3, but the air bubbles and the solution on the inside escape more easily than the circular concave portion by making the planar shape of the concave portion which becomes the bead sitting positions 315 as a square, thus, the loading rate easily increases. The spot array substrate 316 in which the surface-modified beads are arranged on the surface in a two-dimensional array can be obtained by fitting the surface-modified beads 310 in the bead sitting positions 315 formed of a square bottomed hole of the resin substrate 314.

FIG. 9 is a schematic diagram illustrating an example of the resin substrate in which the bead sitting positions formed of a hexagonal bottomed hole are formed in a two-dimensional array on the surface. The resin substrate 317 is similar to the resin substrate shown in FIG. 3, but the planar shape of the concave portion which becomes the bead sitting positions 318 as a hexagon makes it easier for the air bubbles and the solution on the inside to escape than the circular concave portion, thus, the loading rate of the beads easily increases. Further, the hexagonal hole can increase the number of beads which can be loaded per unit area compared with the square hole. The spot array substrate 319 in which the surface-modified beads are arranged on the surface in a two-dimensional array can be obtained by fitting the surface-modified beads 310 in the bead sitting positions formed of the hexagonal bottomed hole of the resin substrate 317.

FIG. 10 is a schematic diagram illustrating an example of the resin substrate in which the columnar pillars are regularly arranged on the surface. A plurality of columnar pillars 322 regularly project to the surface of the resin substrate 320, and the space surrounded by six pillars becomes the bead sitting position 321. By making the space surrounded by the columnar pillars as the bead sitting position, even if the number of beads which can be fine-loaded is the same, the solution flows easily and the beads are easily loaded compared to the case of configuring the bead sitting positions by the hexagonal bottomed hole. A gap between the columnar pillars equals to the configuration which connects between the adjacent bead sitting position and the bead sitting positions with the groove, and has the effect of making the solution flow easily. The gap between the columnar pillars can be considered as the length of the groove shortened to a distance at which the beads are the most densely packed. The spot array substrate 323 in which the surface-modified beads are arranged on the surface in a two-dimensional array can be obtained by fitting the surface-modified beads 310 in the bead sitting positions 321 surrounded by the columnar pillar of the resin substrate 320.

While the resin substrates shown in FIG. 3 to FIG. 10 have different formation states of the bead sitting position, resulting in a difference in the loading rate of the beads, etc., it does not change the essence of the production technique of a low cost spot array substrate which utilizes pattern transfer from the mold of the present invention to the resin and the loading of the beads onto the bead sitting positions set in the two-dimensional array by the pattern. Note that, just as an example, fine-loading, etc., is shown for beads having a diameter of 1 μm, but it is possible to prepare even smaller minute molds. Meanwhile, since the beads having even smaller diameters such as 0.8 μm or 0.6 μm are available, due to the progress of photosensor arrays and optical systems used in the fluorescence observation to be described later, if the pixel number increases and the optical resolution becomes high, it is possible to make practical application of a more highly integrated array having smaller dimensions in accordance with the specifications. According to the present embodiment, a spot array substrate in which the surface-modified beads are arranged in a two-dimensional array at the surface density $6.6 \times 10^6/cm^2$ to $180 \times 10^6/cm^2$ (4.2-μm pitch to 0.8-μm pitch) on the surface can be produced at a low cost. The pitch of 0.8 μm is the limit of the closest filling when 0.6-μm beads are used and corresponds to a surface density of $180 \times 10^6/cm^2$.

Note that, the step of loading the beads which are the array spot material, using the centrifugal force and the magnetic force, is the production step of the spot array substrate and is prior preparation operation when seen from the viewpoint of the user of the analysis device. Thus, it is suitable to preferably supply, to a user, the spot array substrate with this step taken by the manufacturer of the spot array substrate. However, a spot array substrate production kit which includes a resin substrate on which an uneven pattern is formed on the surface and in which a plurality of bead sitting positions are set in a two-dimensional array within the uneven pattern, and surface-modified beads such as the functional group surface-modified beads or oligo DNA surface-modified beads which are loaded onto the bead sitting positions of the resin substrate, and a device which uses a centrifuge (or a rotary machine similar thereto) or a magnet to load the magnetic beads are supplied to the user, and the user may implement the loading step of the material of the array spot himself/herself with only a slight difference in the labor and the cost, or the base member itself is produced at a low cost. Thus, the advantage that a low cost analysis can be implemented by the user is not lost.

Second Embodiment

The filling rate of the beads is preferably high in practical application, and it is desirable to format least 90% of the effective array spot. Therefore, the second embodiment illustrates an example for producing the chip which uses the resin substrate to form a surface-modified spot array such as the functional group spot array and the oligo DNA spot array, and at that time, improving the filling rate of the beads, and implementing measures so that the beads do not fall out during the analysis.

Figure 11:
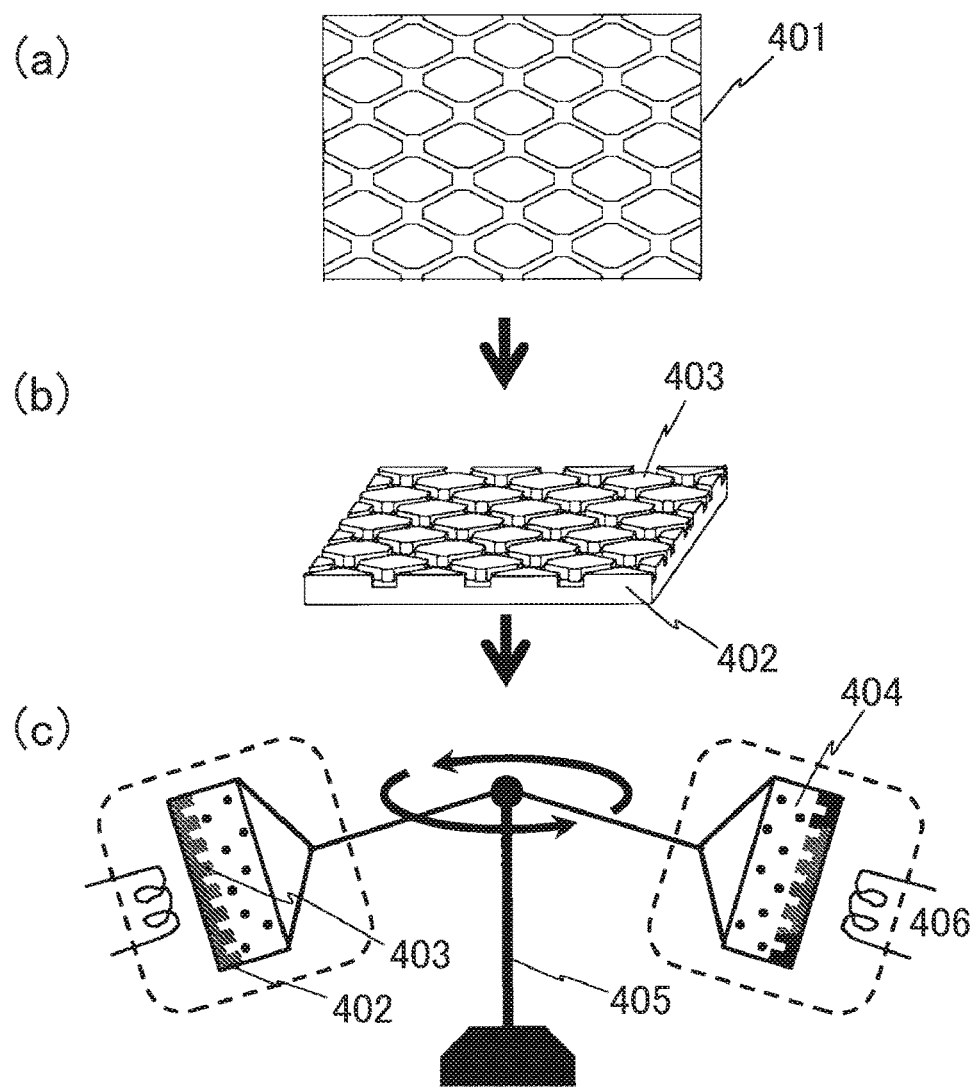
FIG. 11 is a schematic diagram illustrating the production step of the spot array substrate.

FIG. 11 is a schematic diagram illustrating the production step of the improved spot array substrate; FIG. 11(a) illustrates the mold preparation step, FIG. 11(b) illustrates the formation step, and FIG. 11(c) illustrates the spot array formation step. To summarize, the production method of the spot array substrate has a step of preparing the resin substrate in which a mold is used to form the uneven pattern on the surface and a plurality of bead sitting positions are set in a two-dimensional array within the uneven pattern, and a step of loading the surface-modified beads onto the bead sitting positions of the resin substrate, wherein the step of loading the surface-modified beads onto the bead sitting positions of the resin substrate has a first step of loading the surface-modified beads onto the bead sitting positions in a state in which the resin substrate is heated to thermally expand the resin substrate, and a second step of lowering the temperature of the resin substrate, and contracting the resin substrate to make it difficult for the surface-modified beads loaded in the bead sitting positions to fall out. With this method, it is necessary to use the bulk material of the surface-modified beads in which the thermal expansion coefficient is low compared to the material of the resin substrate.

The mold 401 shown in FIG. 11(a) is the same as the mold shown in FIG. 4, which was an Ni electroforming article in which the portion of the densely arranged rhombuses was hollow, with an uneven pattern in which the portion between the adjacent rhombuses protruded. It was confirmed in the first embodiment that the liquid easily flowed into the pattern to which it was transferred and hence the beads were easily fitted. Then, as shown in FIG. 11(b), using this mold, the resin substrate 402 on which the rhombic pattern 403 was formed was produced by the injection molding of a cycloolefin polymer. The surface density of the bead sitting positions set within the uneven pattern of the resin substrate 402 is $6.6 \times 10^6/cm^2$. Lastly, as shown in FIG. 11(c), after the resin substrate 402 which formed the rhombic pattern 403 was once immersed in isopropyl alcohol, and then was replaced with the liquid 404 in which the silica surface amino group modified beads were dispersed while it was carefully observed that no air bubbles were formed, the resin substrate 402 was placed in a centrifuge 405 having a temperature adjusting function 406, and the temperature was raised to 90° C. which was lower than the heat resistance temperature of the resin substrate, while rotating at 3000 rpm for 10 minutes. Then, when the heater of the centrifuge 405 having a temperature adjusting function was turned off and the rotation was continued for an additional 5 minutes, the temperature was reduced to 40° C., and the rotation was terminated. Note that, also in the present embodiment, the beads had an average particle diameter of 1 μm and the variation in the particle diameter of CV10%.

Note that, in the case where the magnetic beads are loaded not by a centrifuge but by a magnetic force, after using the device having a temperature adjusting function which uses a magnet to load magnetic beads and fitting the beads into the bead sitting positions of the uneven pattern while raising the temperature in the same sense, the application of the magnetic force may be turned off after the temperature is reduced, or the resin substrate may be lowered from the device exerting the magnetic force after the temperature is reduced.

The thermal expansion coefficient of a general resin material is in the range from $10^{-5}$ and half or larger to $10^{-4}$[/° C.], and the cycloolefin-based polymer used in the present embodiment also belongs to this category. Because of orders of higher magnitude compared to, for example, the thermal expansion coefficient of $10^{-7}$ of $SiO_2$ which is the main raw material of the silica beads, easy fitting of the beads due to the thermal expansion at raised temperatures and a fixation effect by the tightening of the beads at a lowered temperature can be expected. However, even when the magnetic beads rather than the silica beads are selected, for example, the thermal expansion coefficient of iron and iron oxide is no greater than $10^{-5}$ and half or smaller, and is also smaller than that of the thermal expansion coefficient of the resin. By the selection of the combination of the resin material of the substrate and the material of the beads, even if details are different such as the optimal temperature conditions, the optimal dimension design of, for example, the concave portion of the uneven pattern and the beads constituting bead sitting positions, namely gap design for easy loading and making it difficult to fall out, and the optimal design of the normal tapered angle of the concave portion, if the thermal expansion coefficient of the resin substrate is higher than that of at least the beads, although the range of the effect becomes different, the improvement of the filling rate of the beads and the reduction of the falling out rate can be expected.

The specific dimensions of the expansion amount, for example, in the case of a combination of the silica beads having a diameter of 1 µm and cycloolefin-based polymers, relate to the detailed dimension design of the concave portion. If the diameter (dimension of upper part of the hole) of the inlet of the concave portion (for example, the hole) for loading the silica beads is designed to be slightly larger than 1 µm, and the diameter (dimension of lower part of the hole) of the bottom surface of the concave portion is designed to be slightly smaller than 1 µm as stated in the first embodiment, the beads become easy to load. With respect to the case of using the difference in the thermal expansion coefficient stated in the second embodiment, when the dimensions in the case of raising the temperature to 90° C. are calculated, the hole of the cycloolefin-based polymer substrate becomes approximately 5 nm larger. Meanwhile, the amount of increase of the diameter of the silica beads is two digits smaller than this, thus, it is considered to hardly change at all. Due to the 5-nm increase of the diameter of the hole, the beads are easily loaded into the hole, and fit snugly to a deeper depth. Then, by cooling the cycloolefin-based polymer, the diameter of the hole contracts by 5 nm, thus, it is expected that the beads are securely clamped after loading, and become difficult to fall out.

Whether or not the beads entered the bead sitting positions set in the intersection point of the groove was checked surrounding the rhombic pattern by an electron microscope in order to verify the effect of the improvement measures of the present embodiment. It was verified that the filling rate improved and the amino group modified beads were loaded in 92% of all the bead sitting positions. It is assumed that the resin expanded more than the beads by increasing the temperature to 90° C., and as a result, the beads became easy to fit and the loading rate of the beads improved.

Next, in the same manner as the first embodiment, after running the aqueous solution of the reagent for analysis for 12 hours while repeating the temperature control (10 to 70° C.) for controlling the enzyme reaction in order to simulate the use in the subsequent analysis, the beads which entered the bead sitting positions were again checked by an electron microscope, and as a result, it was found that the filling rate was maintained at 92% of all. It is considered that when the improvement measures were used, the beads were fit and securely immobilized, and the beads became difficult to fall out. Compared with the first embodiment, an additional temperature adjusting function is necessary in the device which uses a centrifuge or a magnet to load the magnetic beads, but the increase of the cost of production is not large. It is considered that, compared to using an Si wafer for all of the chips and producing by a semiconductor process, the effect of the addition of the temperature adjusting function to the cost increase is remarkably small.

For comparison, the material of the substrate was made from Si, and the evaluation of the loading and the falling out of the beads was performed in the same manner. As stated above, when the material of the substrate was a cycloolefin-based polymer, the dimensions of the concave portion of the bead sitting positions increased due to the temperature increase of the substrate and the beads became easy to fit. However, when Si is the material of the substrate, the thermal expansion coefficient is $10^{-6}$ and half or smaller, thus, the dimensional change of the concave portion of the bead sitting positions is small (Si hardly expands compared to resin, even if the temperature increases). Further, the dimensions of the silica beads hardly change. Therefore, it is considered that a sufficient effect to make the beads fit easily and become difficult to fall out cannot be obtained by controlling the temperature.

Figure 12:
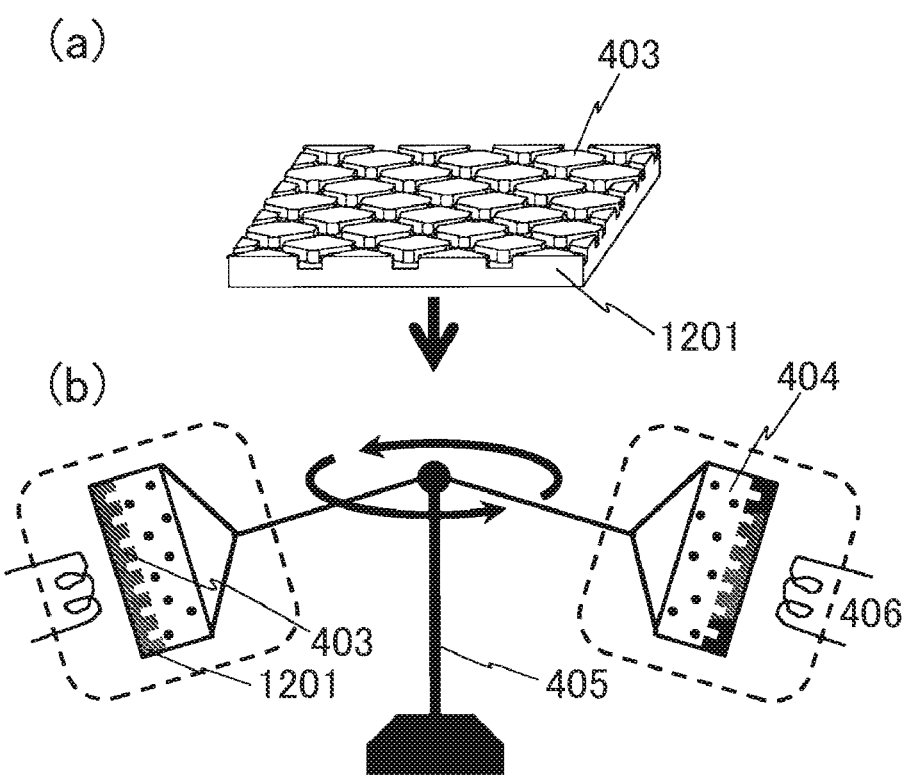
FIG. 12 is a schematic diagram illustrating the production step of the spot array using the Si substrate.

The procedures of the evaluation are shown in FIG. 12. In FIG. 11, the resin substrate 402 on which the rhombic pattern 403 shown in FIG. 11(b) was formed by the Ni electroforming mold 401 shown in FIG. 11(a) was used in the evaluation of the loading of the beads, but when preparing the Ni electroforming mold 401 of FIG. 11(a), an Si substrate 1201 having the same surface formation as the Si mold used as the master was used in the evaluation. As illustrated simply in FIG. 1, the Si concave minute mold (master) 202 has the same surface formation as the resin substrate 204 which forms the array 205 of the concave portion, and only the materials are different.

A semiconductor process (lithography, dry etching, asking) in the same manner as when preparing the mold was used to micromachine the Si wafer, and as shown in FIG. 12(a), the Si substrate 1201 having the same surface formation as the Si concave minute mold (master) was prepared. The same rhombic pattern 403 as the surface of the resin substrate 402 shown in FIG. 11(b) was formed on the surface of the Si substrate 1201. Then, as shown in FIG. 12(b), the Si substrate 1201 was once immersed in isopropyl alcohol, and then was replaced with the liquid 404 in which the silica surface amino group modified beads were dispersed while it was carefully observed that no air bubbles were formed, the Si substrate 1201 was placed in a centrifuge 405 having a temperature adjusting function 406, and the temperature was raised to 90° C. which is lower than the heat resistance temperature of the resin substrate, then the Si substrate 1201 was rotated at 3000 rpm for 10 minutes. When the heater of the centrifuge 405 having a temperature adjusting function was turned off and the rotation was continued for additional 5 minutes, the temperature was reduced to 40° C. and the rotation was terminated. In the present embodiment also, the beads had an average particle diameter of 1 µm and the variation in the particle diameter was CV10%.

It was checked by an electron microscope whether or not the beads entered the bead sitting positions set at the intersection point of the grooves surrounding the rhombic pattern, and it was verified that the filling rate of the beads decreased compared to when the material of the substrate was a cycloolefin-based polymer and that the amino group modified beads were loaded into 70% of all the bead sitting positions. Further, after running the aqueous solution of the reagent for analysis for 12 hours while repeating the temperature control (10 to 70° C.) for controlling the enzyme reaction in order to simulate the use in the subsequent analysis, the beads which entered the bead sitting positions were again checked by an electron microscope, and as a result, it was found that the filling rate further decreased to 60% of all. Thus, it was found that when the substrate material was made from Si, the effect of the beads becoming easy to fit due to the thermal expansion caused by an increase in the temperature of the substrate, and the effect of the loaded beads being tightened and becoming difficult to fall out due to the decrease of the temperature of the substrate could not be obtained.

Above, in the method for producing the surface-modified spot array in which a resin substrate uses a mold to form an uneven pattern on the surface and in which a resin substrate with a plurality of bead sitting positions set in a two-dimensional array within the uneven pattern is used, it was shown that not only the material cost and the cost of production were cheaper but the property that the resin has a high thermal expansion coefficient was actively utilized to improve the loading rate of the beads by the temperature adjusting function and reduce the falling out ratio of the beads, namely, the yield of the array spot production could be improved.

Note that, in the same manner as the first embodiment, it is desirable that the spot array substrate is supplied to the user as a finished product by the manufacturer. However, a device including the spot array substrate production kit which includes the molded substrate and the beads which are the material of the array spot and a centrifuge having a temperature adjusting function (or a rotary machine similar thereto) or a temperature adjusting function which uses a magnet to load the magnetic beads is supplied to the user, and the user may implement the loading step of the material of the array spot himself/herself and produce the base member itself at a low cost. Thus, the advantage that a low cost analysis can be implemented by the user is not lost.

Third Embodiment

Next, the third embodiment used the resin substrate to produce a chip which formed the functional group spot array or an oligo DNA spot array, and especially at that time, the effect of the chemical bond at a fixed location of the beads and the effect of narrowing the particle size distribution of the beads were examined as other measures for raising the filling rate of the beads and preventing the beds from falling out during the analysis.

Figure 13:
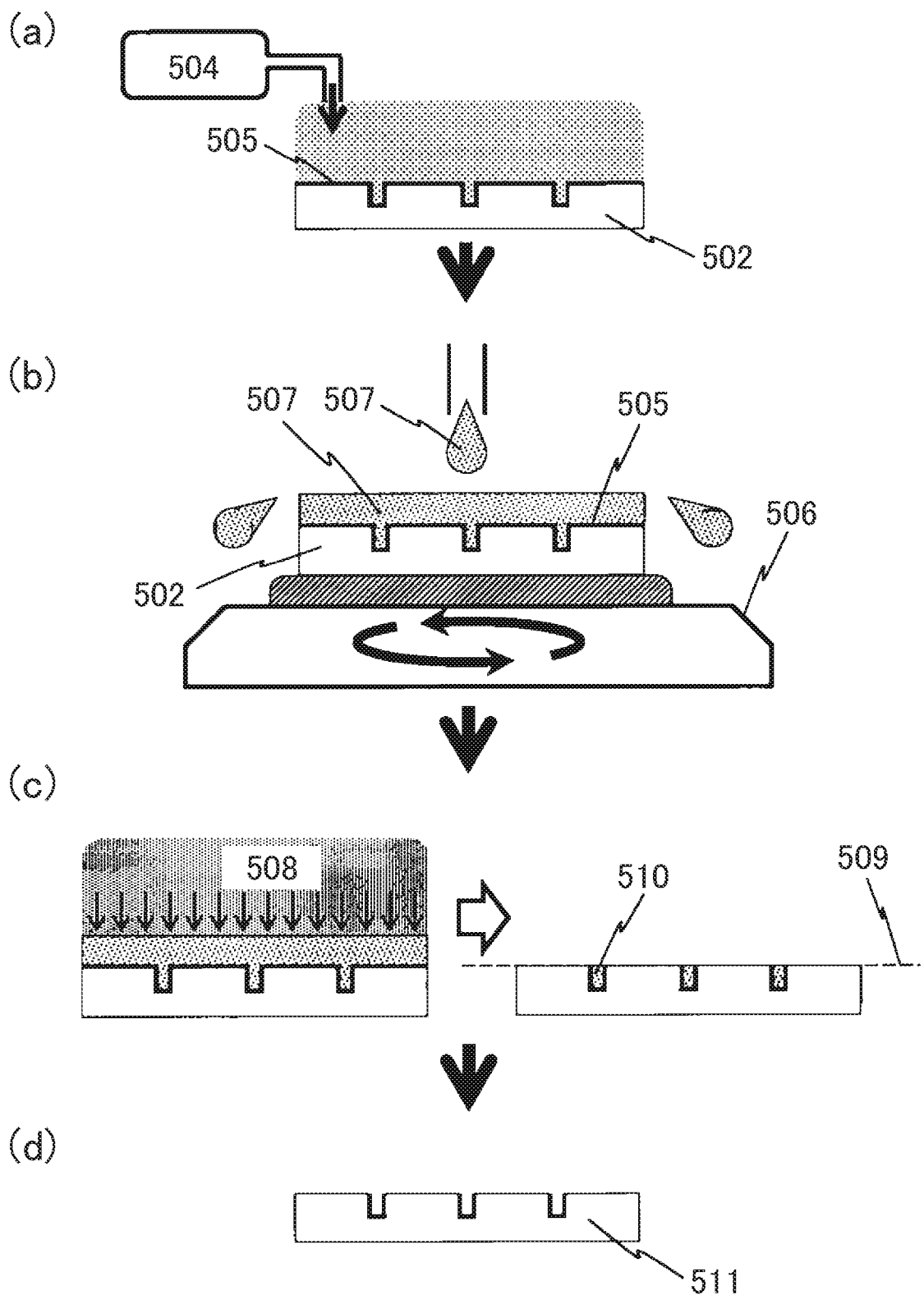
FIG. 13 is a schematic diagram illustrating the production step with addition of a chemical bond formation step.

FIG. 13 is a schematic diagram illustrating the production step of the spot array substrate in which a step of forming the chemical bond is added in order to examine the effect of the chemical bond in the fixed position of the beads. The mold preparation step, the formation step and the spot array formation step which comes last are the same as in the second embodiment, and thus, an explanation is omitted. FIG. 13(a) shows the gas-phase CVD step following the formation step, FIG. 13(b) shows the resist resin spin coating step, FIG. 13(c) shows the $O_2$ dry etching step, and FIG. 13(d) shows the removal step of the resist resin for protection. To summarize, it is a spot array device production method which uses the substrate in which the bead sitting positions are surface-modified in advance so that an uneven pattern can be formed in a resin with a mold, and the chemical bond can be formed when fitting the beads modified with a functional group or oligo DNA in bead sitting positions having an uneven pattern.

In the present embodiment, while there is an increase in the number of steps, the following four steps were added to form the chemical bond after producing the resin substrate with a plurality of bead sitting positions set in a two-dimensional array within the surface uneven pattern by the formation steps shown in the second embodiment.

First, as shown in FIG. 13(a), an epoxy-based silane coupling agent 504 was used in a precursor to form an epoxysilane film 505 in the resin substrate 502 which formed the rhombic patterns by injection molding by gas-phase CVD, and an epoxy group was formed on the surface. Next, as shown in FIG. 13(b), the resist resin 507 which is completely soluble in acetone was coated on the surface of the resin substrate 502 on which the epoxysilane film 505 was formed by a spin coater 506. Next, as shown in FIG. 13(c), an RIE (Reactive Ion Etching) device was used and the upper surface 509 of the substrate was etched back by $O_2$ plasma 508 until it was exposed. When the dry etching was completed, the upper surface of the rhombic pattern was exposed to the cycloolefin-based polymer while the resist resin 510 which entered the grove remains. Therefore, the inner surface of the groove is in a state in which the epoxy group is covered by and protected in the resist resin. Next, as shown in FIG. 13(d), by removing with acetone the resist resin which covers the epoxy group within the groove, the cycloolefin-based polymer substrate 511 of the rhombic pattern in which only the inner surface of the groove modified by an epoxy group was produced. Note that, the cycloolefin-based polymer resin substrate does not dissolve in acetone, thus, an example in which the coated resist resin is removed by dissolving in acetone is shown. But in the example, the resin substrate material is dissolved in acetone, thus, with this in mind, it is necessary to select a combination of a protective resin and a solvent appropriate for the substrate material. Conversely, there are resins having a high organic solvent resistance such as a cycloolefin-based polymer exists, thus, it is also possible to use other resist stripping agents for the removal of the resist resin, and the solvent for resist stripping is not limited to acetone.

After adding these 4 steps, finally, as the evaluation of the filling rate of the beads, after the cycloolefin-based polymer substrate 511 of the rhombic pattern in which only the inner surface of the groove modified by the epoxy group was immersed in isopropyl alcohol once in the same manner as the case of FIG. 11(c), and then was replaced with the liquid in which the silica surface amino group modified beads were dispersed while it was carefully observed that no air bubbles were formed. Then, the substrate 511 was placed in a centrifuge having a temperature adjusting function, and the temperature was raised to 90° C. while rotating at 3000 rpm for 10 minutes. Then, when the heater of the centrifuge having a temperature adjusting function was turned off and the rotation was continued for an additional 5 minutes, the temperature was reduced to 40° C. Thus the rotation was terminated. Note that, even in the evaluation of the effect of the chemical bond, the beads had an average particle diameter of 1 μm and the variation in the particle diameter was CV10%.

Note that, when the magnetic beads are loaded using a magnet and not a centrifuge, it suffices that the device having a temperature adjusting function for loading the magnetic beads using a magnet is used in the same manner, and after the beads are fit upon raising the temperature, the temperature is reduced and the application of the magnetic force is turned off, or, the temperature is reduced and the loaded beads are removed from the device influencing the magnetic force.

In the evaluation, therefore, it was estimated that a chemical bond would form by the amino group of the amino group modified beads which is an example of the spot array material and the epoxy group on the inside of the groove of the substrate, and it was anticipated that the filling rate of the beads would furthermore increase. In order to verify the effect of the chemical bond, whether or not the beads entered the bead sitting positions set in the intersection point of the groove surrounding the rhombic pattern was checked by an electron microscope. It was verified that the filling rate further improved, and the amino modified beads were loaded into 96% of the bead sitting positions among the entirety. It is assumed that the filling rate of the beads improved by the addition of an immobilization effect due to the chemical bond.

Next, as in the first and second embodiments, after repeating the temperature control (10 to 70° C.) for controlling the enzyme reaction while running the aqueous solution of the reagent for analysis for 12 hours in order to simulate the use in the subsequent analysis, the beads which entered the bead sitting positions were again verified by an electron microscope, and as a result, the filling rate decreased slightly, and was 94% of all of them. While a reduction of 2% was observed, a high filling rate of the beads and a high bead residual ratio (=the filling rate–the falling out rate) were obtained by addition of the immobilization effect due to the chemical bond, compared to the case without the immobilization effect. Note that, other than the epoxysilane film formed by the epoxy-based silane coupling agent, for example, an isocyanate silane film and the like formed by an isocyanate-based silane coupling agent can be used as the material which can form a chemical bond with the amino group modified beads. An examination was conducted on a trial basis in the same manner, and as a result, the beads having a filling rate of 95% which is almost the same as the case of the epoxysilane film could be obtained, and, a bead residual ratio of 94% could be obtained after a 12-hour run which simulated the analysis.

Even in the case where either functional group is used, it can be interpreted that the chemical bond increases the ability to maintain the beads in the bead sitting positions on the substrate. However, when compared with the first and second embodiments, there is an increase of the 4 steps of FIG. 13(a) to (d), thus, the cost of production will increase to some degree. However, at least when compared to producing all the chips by a semiconductor process using an Si wafer, fine patterning (lithography) is not used for all of the chips, and thus, it is a method which can produce the chips at a low cost.

Note that, also in the method which uses the effect by the chemical bond, it is desirable that the spot array substrate is supplied to the user as a finished product by the manufacturer, in the same manner as the First and Second Embodiments. Certainly, it is possible to be in a form in which the user implements the fitting step of the array spot material, and in this case, the base member itself is produced at a low cost, thus, the advantage that the analysis can be implemented at a low cost is not lost. However, in the case of the present embodiment, when supplying the set of the molded substrate, the beads which become the array spot material, and the device having a temperature adjusting function which uses the centrifuge having the temperature adjusting function and the magnet to load the magnetic beads, from the viewpoint of the protection of the functional group (in the present embodiment, the epoxy group, or, the isocyanate group) in a positon in which the beads of the formed substrate are immobilized, it is safer to supply to the user with a cover of the resist resin attached which protects the functional group on the inside of the groove. In this case, the user must first remove the resist resin with an organic solvent (acetone, etc.), and this increases the work steps and increases the complexity for the user compared to the First and Second Embodiments.

However, a specific problem was discovered when the chemical bond in the present embodiment was used. As stated above, with respect to the bead sitting positions set in the intersection point of the groove surrounding the rhombic pattern, while the results that the loading rate of the amino group modified beads was 96% and that the bead residual ratio after simulating the analysis with a 12-hour run was 94% were good, and the nonspecific adsorption of the amino group modified beads was found here and there on the upper surface of the rhombic pattern irrespective of the bead sitting positions, namely, on the surface in which the cycloolefin-based polymer was exposed by removing the film forming the functional group by dry etching. In the first and second embodiments, the surface of the cycloolefin-based polymer substrate with an uneven pattern formed on the surface by injection molding and thermal deformation (thermal imprint) maintains the hydrophobicity, and nonspecific adsorption was not a problem. However, the surface of the substrate of the cycloolefin-based polymer of the present embodiment is the surface of the cycloolefin-based polymer which was exposed again after forming another film thereon and removing the film by $O_2$ plasma etching. Therefore, it was assumed that, when the cycloolefin-based polymer was exposed by, for example, dry etching, the surface of the cycloolefin-based polymer was a state of the surface functional group which was different from the usual surface of the cycloolefin-based polymer such as O which was bound to the C atom on the surface of the cycloolefin polymer to form, for example, an —OH group bonded to C on the surface due to the $O_2$ plasma used in dry etching.

Therefore, after the $O_2$ dry etching step of FIG. 13(c), a gas-phase CVD step with a fluorocarbon-based ($CF_x$-based) silane coupling agent as a precursor was added as a nonspecific adsorption measure. At this point in time, the functional groups of the bead sitting positions are covered by the resist resin, thus, after adding the step, if acetone is used to remove the protective resist resin as shown in FIG. 13(d), the desired functional group (in the present embodiment, an epoxy group, or, an isocyanate group) is exposed in the bead sitting position, and flat portions other than this (if a rhombic pattern, the rhombus-shaped upper surface) will result in a substrate on which a hydrophobic surface treatment is performed so that there is no nonspecific adsorption.

The bead loading test and the falling out test which used the temperature adjusting function were performed to this substrate in the same manner, and the good results such as the loading rate of the amino group modified beads being 96% and the bead residual ratio after simulating the analysis with a 12-hour run being 94% were unchanged. Further, nonspecific adsorption was not observed in the range observed by the electron microscope. It is assumed that even in the same resin substrate, if surface oxidation and the like occurs due to a plasma treatment, etc., the surface state will change, and in this case, it was found that the surface having similar characteristics as the original resin material (hydrophobic plastic) surface could be formed by performing a fluorocarbon-based, etc., hydrophobic surface treatment, and could be used in the prevention of nonspecific adsorption.

However, apart from the nonspecific adsorption on the surface (if a rhombic pattern, the rhombus-shaped upper surface) exposed to $O_2$ plasma due to the dry etching of the cycloolefin-based substrate, the beads having a small particle size were discovered immobilized in a position which was not an intersection point within the groove surrounding the rhombic pattern, although it was not frequent. As shown in FIG. 4, in a rhombic pattern, the beads can enter the grooves surrounding the rhombuses and the position of the intersection point of the groove by design, but the groove which is not an intersection point has a narrower width than the bead diameter, and thus, is designed so that the beads cannot enter. However, since there is actually a distribution of particle sizes in the beads, it is considered that the beads in which the dimensions excessively deviate in the direction which is smaller than the average diameter are chemically bonded, or, physically fitted with the epoxy group or the isocyanate group on the inside of the groove.

Taking the variation in the particle diameter of the beads into consideration, it is also possible to avoid the above problem by changing the groove width to be more narrow, but other than that, by slightly changing the production method shown in FIG. 13, the epoxy group or the isocyanate group can remain only in the intersection point within the groove. Specifically, the epoxy group or the isocyanate group are not protected with the resist resin cover such as by the resist resin spin coating step shown in FIG. 13(b), and in place of this step, as an example, the method for loading the silica beads which were not chemically modified in the intersection point of the grooves surrounding the rhombic pattern by the centrifuge, and using the cover with the silica beads in the protective mask of the epoxy group or isocyanate group, can be considered. After physically fitting the silica beads in the intersection point of the grooves surrounding the rhombic pattern, the RIE device is used in the same manner as FIG. 13(c) and $O_2$ plasma is used to remove the epoxy groups or the isocyanate groups other than the portions hidden in the beads by etching back. Lastly, the substrate in which the spot of the epoxy group or the isocyanate group was removed can be prepared in only the bottom part of the intersection point of the grooves surrounding the rhombuses by flipping over the substrate and placing it in the centrifuge in a state in which the temperature is increased to 90° C., and removing the beads by the centrifuge. The beads having a small particle size immobilized in the portion within the groove which is not an intersection point position could be made to zero in the verified field of view by changing the design to make the groove dimension narrow. However, this method does not require resist resin spin coating, but instead requires the addition of the two steps of the loading of the silica beads and the removal of the silica beads, thus, while the function for preventing the immobilization within the groove improves, the production steps increase.

Therefore, further simplification of the steps for forming the epoxy group or the isocyanate group for the chemical bond was examined as another examination of the method utilizing the effect of the chemical bond. This is not a complicated method such as removing an epoxy group or an isocyanate group of the unnecessary portion (the upper surface of the rhombic pattern) after performing gas-phase CVD or the resist resin coating (or, the loading of the silica beads as the protective mask) as shown in FIG. 13, and a simple method in which the treatment by only a silane coupling agent within the groove surrounding the rhombic pattern and the intersection point of the groove was examined.

Figure 14:
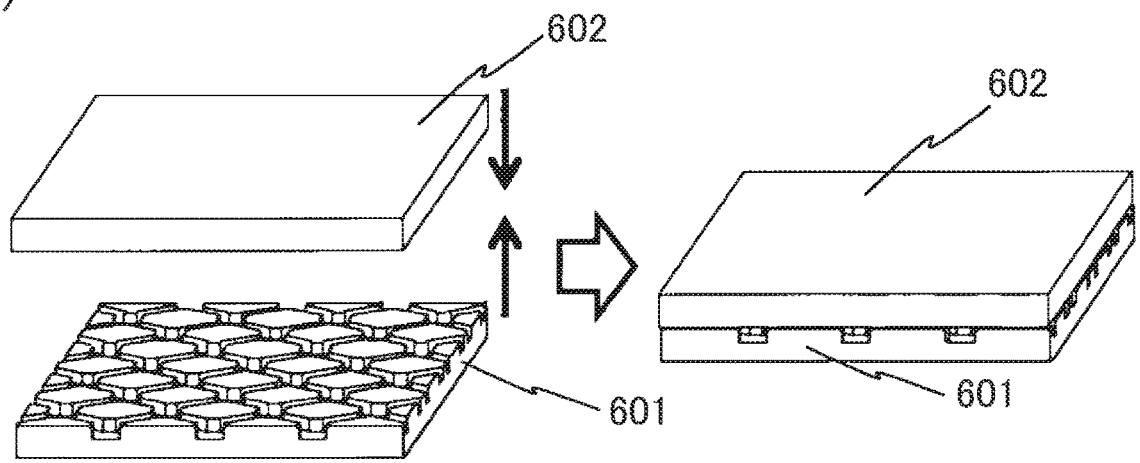
FIG. 14 is an explanatory drawing of a method for easily adding a chemical bond formation step.
Figure 14:
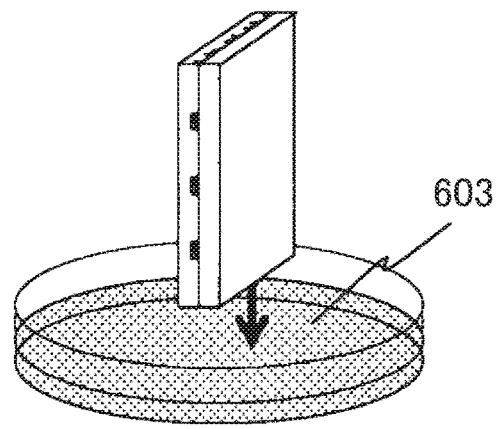
Figure 14:
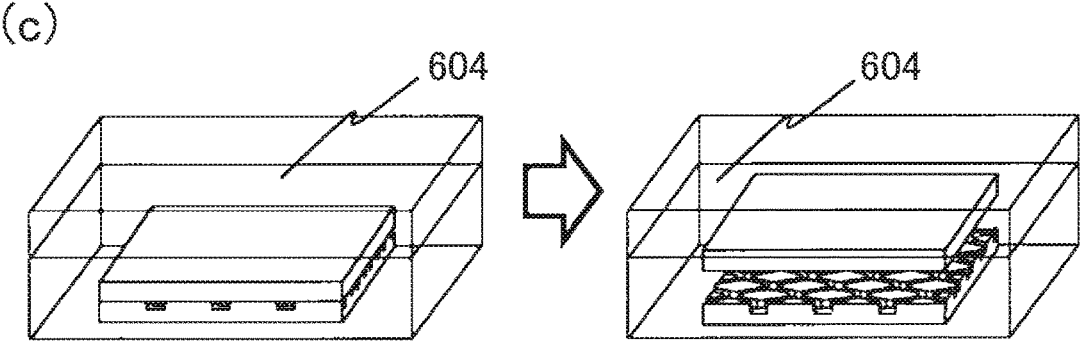

FIG. 14 is a schematic diagram illustrating the simple procedures of the method. FIG. 14(a) illustrates the step of adhering with a flat plate, FIG. 14(b) illustrates the surface treatment step within the groove by the capillary phenomenon, and FIG. 14(c) illustrates the washing step. First, as shown in FIG. 14(a), the pattern surface of the cycloolefin-based polymer substrate 601 on which the rhombic pattern was formed is tightly adhered with the flat plate 602. Next, as shown in FIG. 14(b), the end is immersed in an epoxy-based or an isocyanate-based silane coupling agent (liquid) 603. By this step, the silane coupling agent enters the inside of the groove through the rhombic pattern. Then, as shown in FIG. 14(c), a substrate 601 was adhered with a flat plate 602, immersed in the liquid 604 for washing, the excess silane coupling agent on the inside and outside of the groove was washed off, and replaced with as much of the liquid for washing as possible, and furthermore, the flat plate 602 was removed to thoroughly wash the excess silane coupling agent, so that only the silane coupling agent bound with the substrate remained on the surface within the groove.

The substrate prepared as such was evaluated, and as a result, it was found that 95% of the amino beads could be loaded in almost the same manner as the substrate prepared by the production method of FIG. 13. Further, on a trial basis, one drop of the silane coupling agent was directly dropped on the end of the rhombic pattern without using the flat plate 602, and in this case, the silane coupling agent could enter the grooves of the rhombuses through the rhombic pattern due to the capillary phenomenon, but in the portion where one drop dripped, the silane coupling agent was greatly extruded and was also attached to the planar part of the upper surface of the rhombic pattern other than the groove.

Other than forming a film with the liquid silane coupling agent by the gas-phase of the vacuum device, a method which can modify the inside of the groove by the capillary phenomenon in the liquid state could be confirmed by a manual operation. If the adhesion with the flat plate and the extrusion at the portion in which the drop is dripped is properly prevented, the amino bead sitting positions can be chemically modified by the treatment with a silane coupling agent in a liquid state, and the filling rate of the amino beads the filling rate can be improved.

Changing the viewpoint slightly, lastly, the effect of the narrowing of the particle size distribution of the beads was examined as another measure for further improving the filling rate of the beads and the residual ratio of the array spot material. First, it is assumed that the reason why the filling rate of the beads was improved by the method which uses the effect of the chemical bond stated above and the reason why the residual ratio of the beads decreased by only 2% after being used to simulate the analysis are that, it was deduced that due to the extent of the particle size distribution of the beads, the beads which were considerably smaller than the average particle diameter were not physically fitted tightly but were immobilized only by chemical bonding, and the beads fell out while used to simulate the analysis, thus, it was essential to properly arrange the particle size of the beads to narrow the distribution. Further, it is anticipated that the beads which are immobilized in a position which is not the intersection point within the groove can be eliminated by the narrowing of the particle size distribution of the beads. Following this consideration, the same treatment as in FIG. 11 of the second embodiment was performed without using the effect of the chemical bond shown in FIG. 13. In the spot array formation step, the temperature adjusting function is also used to perform the fitting of the beads in the same manner as the second embodiment. However, this method is different from the second embodiment, in that CV3% was used as the variation in the particle diameter of the beads.

To verify the effect of the narrowing of the particle size distribution of the beads, whether or not the beads entered the bead sitting positions set in the intersection point of the groove surrounding the rhombic pattern was checked by an electron microscope, and it was verified that the filling rate improved compared to the case of CV10% shown in the second embodiment, and the amino group modified beads were loaded into 95% of the bead sitting positions among the entirety. Further, the bead residual ratio after simulating the analysis with a 12-hour run remained 95%, and in addition, nonspecific adsorption was not observed at all in the range observed by the electron microscope. It is considered that as a result of changing from CV10% to CV3%, the ratio of the beads that are too large to be loaded for being too large compared to the average and the beads which can be loaded, but immediately fall out for being too small compared to the average decreased to improve the dimensional compatibility with the bead sitting positions of the resin substrate, and the filling rate of the beads and the residual ratio became large.

In the third embodiment, in order to further improve the results of the 92% filling rate of the beads obtained by the second embodiment and the bead residual ratio of 92% after the analysis simulation, a bead filling rate of 96% and a bead residual ratio of 94% were obtained by the combined use of chemical bonding at the bead sitting positions and a hydrophobic treatment for preventing non-specific adsorption. However, when the particle size distribution of the beads was reduced from CV10% to CV3%, the filling rate of the beads became 95%, and the bead residual ratio became 95%. Only the beads having a narrow particle size distribution were selected during the production process, and have a higher cost than the beads having a wide particle size distribution, but it is considered that, at least, due to the production process for subjecting each mass production substrate to film forming, etching and the like to perform a surface-modified treatment for the chemical bond and a non-specific adsorption preventive treatment, the increase of the cost is low, and the production process is also remarkably simple.

Examples regarding several methods which form the array spot at a formation rate of 90% or more were shown above, and the relative merits such as the cost of production were examined. Therefore, there are several implementation methods, but the following Fourth and Fifth Embodiments show examples, among the methods, using "the production steps as the second embodiment, but a substrate having an array spot formation rate of 95% produced using the CV3% beads" illustrated at the end of the third embodiment to perform the analysis of a nucleic acid polymer, and a decoding of the base sequence.

Fourth Embodiment

The fourth embodiment illustrates an example of the analysis which used the flow cell which incorporated the spot array substrate.

Figure 15:
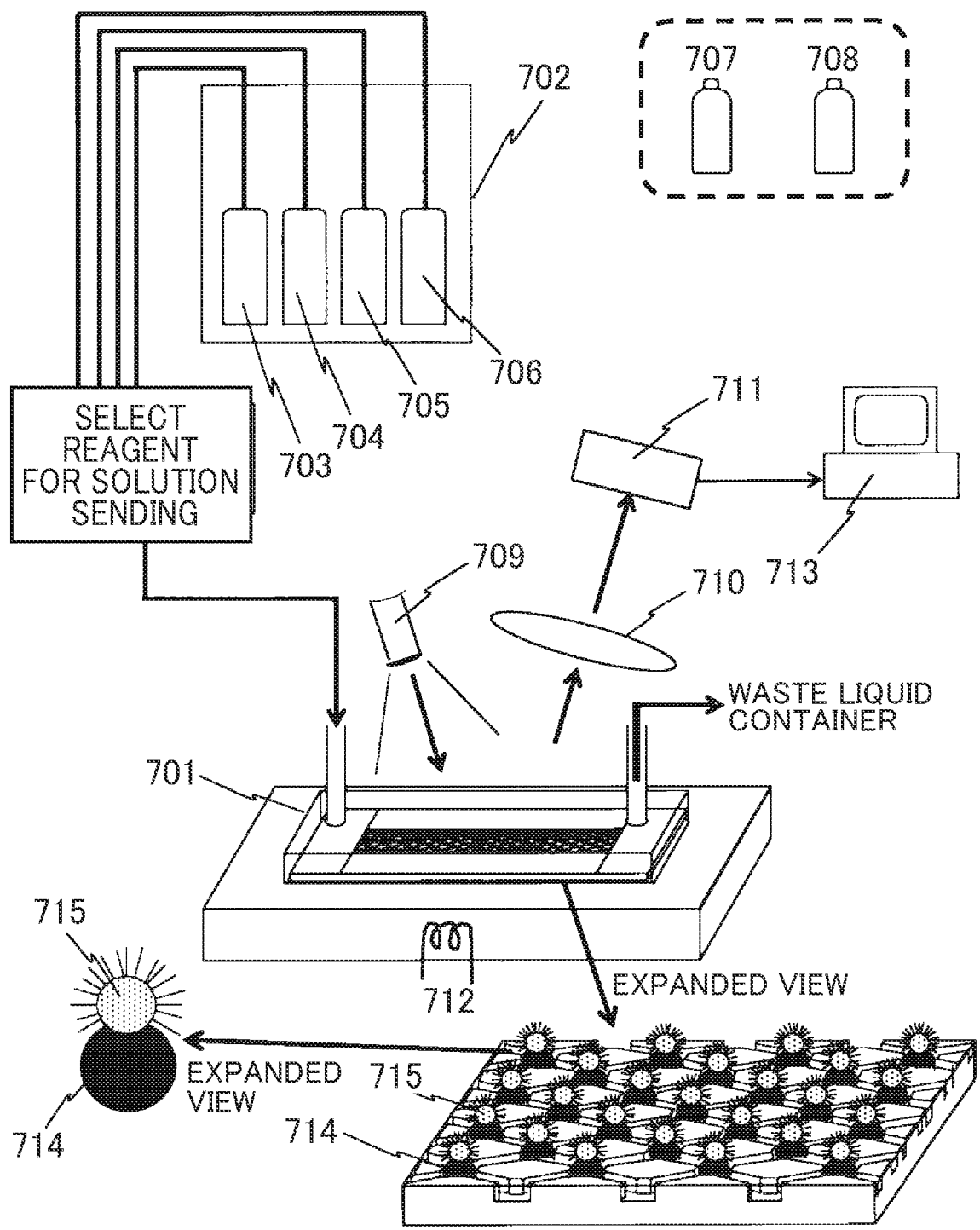
FIG. 15 is a schematic drawing illustrating a configuration example of the nucleic acid polymer analysis device.

FIG. 15 is a schematic drawing illustrating a configuration example of the nucleic acid polymer analysis device used in the present embodiment. The spot array substrate made of resin was incorporated in the flow cell 701. The solution which was introduced through the solution inlet of the flow cell 701 soaks the surface of the spot array substrate, and is discharged from the solution outlet to a waste liquid container. The bead sitting positions of the cycloolefin substrate in which the uneven pattern was formed by the convex portion of the densely arranged rhombuses and the shape of the groove surrounding the convex portion were used as the spot array substrate, namely, the amino group surface-modified beads 714 are fitted in advance by the centrifugal force in the intersection point position of the groove surrounding the rhombic pattern. The basic material of the beads is silica. Further, the beads used a silica in which the particle size distribution is CV3%, and the filling rate of the beads into the bead sitting positions of the spot array substrate is 95%. The template DNA having an unknown sequence in at least the portion which is the object for analysis was amplified in advance on the beads by emulsion PCR, the amplified template DNA was immobilized on the array spot surface-modified with an amino group and analyzed by the fluorescence measurement, and the base sequence was decoded.

Note that, as stated in the First to Third Embodiments, it is possible that the resin substrate (for example, the form arranged in the flow cell) in which the bead sitting positions of the two-dimensional array were set with the uneven pattern formed on the surface and the beads (for example, the liquid in which the beads were dispersed) surface-modified with a functional group (in the present embodiment, an amino group) are supplied separately to the user, and the user fits the beads in the bead sitting positions of the substrate to form the functional group spot array substrate and uses this substrate.

The temperature control of the flow cell 701 is possible by the temperature adjusting function 712. Further, the reaction reagent unit 702 which supplies several reaction reagents is installed and held at a low temperature where the enzyme reaction does not progress within the reagent, and is connected to the flow cell 701 with piping tubes. In the present embodiment, four types of reagents 703 to 706 can be supplied by the reaction reagent unit 702. The reagent 703 is introduced to the bead surface on which the template DNA having an unknown sequence in at least the portion which is the object for analysis modified by the oligo DNA (known sequence) in advance, and includes the beads (beads 715 which form the replica of the template DNA on the surface by emulsion PCR) amplified by emulsion PCR. The reagent 704 includes dATP-fluorescent dye 1, dGTP-fluorescent dye 2, dCTP-fluorescent dye 3, d-TTP-fluorescent dye 4, a known sequence (oligo DNA) used in the bead-side fixed terminal of the beads for emulsion PCR and a complementary primer, and the elongation reaction enzyme. The reagent 705 is a dye bond cleaving reagent which cleaves the bond between the four types of dNTP and the fluorescent dye. The reagent 706 is an electrolyte solution.

Further, isopropyl alcohol 707 and the electrolyte solution 708 which is an equivalent of the reagent 706 were separately prepared. These solutions are injected into the flow cell by a pipette. Isopropyl alcohol 707 is used in the solution replacement within the flow cell, and another alcohol such as ethyl alcohol may be used.

A light source 709 for generating the excitation light for exciting each type of fluorescent dye contained in the reagent 704, an optical system 710 for measuring the fluorescence from the fluorescent dye, and a photodetector array 711 are arranged above the flow cell 701. The illumination of the excitation light and the fluorescence detection are possible even if with a non-transparent substrate, and, if a transparent thin substrate is used, the excitation and the detection are possible even from below the substrate, thus, in the present embodiment, the vertical arrangement of the optical system and the detector is not specifically limited. If the temperature adjustment, photoexcitation, and fluorescence observation can be performed, the optical system can be arranged either above or below the flow cell. Further, the optical signals received by the photodetector array 711 are converted to electric signals and transferred to the analyzing device 713. The analyzing device 713 performs analyses such as the discrimination of the bases from the transferred signals and the connecting of fragment data, and decodes the base sequence of the nucleic acid polymer.

It is well known that, as the fluorescent dye which can be used in the fluorescent dyes 1 to 4 contained in the reagent 704, Alexa488, Cy3, Cy5, Cy5.5, Alexa555, Alexa647, Alexa680, dN6G (dichloro-rhodamine 6G), dN110, dTAMNA (dichloro-carboxyteetramethyl-rhodamine), dROX (dichloro-carboxy-X-rhodamine), etc., and various fluorescent dyes are commercially available, and a suitable dye can be selected so that the wavelengths do not partially overlap. Further, it is also well known that selecting at least one type or more suitable wavelengths as the wavelengths of a light source 709 for efficiently exciting the fluorescent dye by the selection of these dyes.

In the present embodiment, first, isopropyl alcohol 707 was injected through the inlet of the flow cell 701 by a manual operation using a pipette and after verifying that there were no air bubbles, the isopropyl alcohol 707 was replaced with the electrolyte solution 708 by a manual operation using a pipette. The operation for replacing from alcohol to the electrolyte solution 708 may also be performed by automatic solution sending, and, in some cases, it is also possible to use the method, etc., for substituting from an alcohol to an electrolyte solution 708 on the flow cell maker side and fill the liquid in advance to supply to the user. In any event, next, the flow cell 701 was set in the nucleic acid polymer analysis device with the electrolyte solution 708 filling the cell and the air bubbles removed.

Next, the reagent 703 containing the beads 715 which formed the replica of the template DNA on the surface was automatically injected into the flow cell 701 by a solution sending unit, the solution sending was stopped once in this state, the reagent 703 was set to the optimal temperature, left standing for three hours, and immobilized on the amino group-modified spot array. The spot array material (amino group surface-modified beads 714) of which 95% of all of the bead sitting positions were surface-modified with the amino group during production was embedded in the cycloolefin substrate incorporated in the flow cell 701, but the beads 715 which formed the replica of the template DNA by emulsion PCR could be immobilized on the surface in 92% of the spots among this 95%. 3% of the spots were not immobilized. Then, a suitable temperature was set, the reagent 704 was supplied to the flow cell, hybridized with a primer, and the elongation reaction was conducted with an enzyme. At this time, since the dNTP within the reagent was terminated by the fluorescent dye, after conducting the elongation reaction on the first base type of the template DNA, the reaction was stopped. Then, the excitation light was illuminated by the light source 709, and the fluorescence emitted at this time was measured by the optical system 710 and the photodetector array 711.

Figure 16:
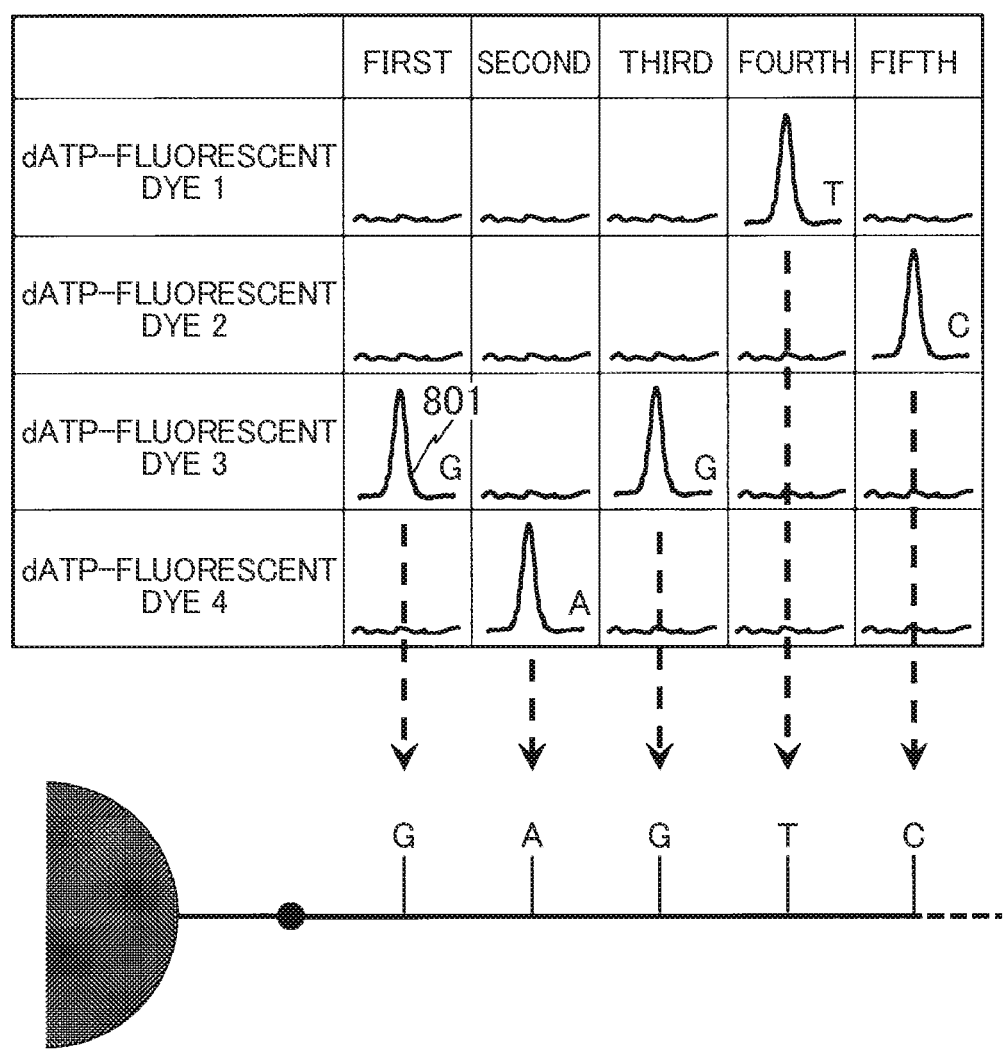
FIG. 16 is a graph illustrating an example of the measurement result of the fluorescence.

FIG. 16 shows an example of the measurement result of the fluorescence emitted by exciting with the light source 709 after conducting an elongation reaction in one of the array spots on the cycloolefin substrate incorporated in the flow cell 701. Since the fluorescence of the fluorescent dye 3 bound to dCTP was verified in the first data 801, the first base was decoded as G. Then, the dye was cleaved at a suitable temperature by the reagent 705 including the dye bond cleaving reagent, and after washing the liquid within the flow cell containing the cleaved dye with the electrolyte solution of the reagent 706, the reagent 704 was automatically injected again, and the second or subsequent analysis of the bases was repeated in the same manner. As shown in FIG. 16, the measurement was performed until the fifth time (until the fifth base), and as a result, the sequence until the fifth base from the connection terminal of the oligo DNA on the beads for emulsion PCR in one of the selected array spots could be decoded as GAGTC.

Note that, in the present embodiment, it is necessary that one bead which replicates the template DNA by emulsion PCR in advance is the bead in which one type of template DNA is replicated. In emulsion PCR, with the exception that one type of template DNA is replicated on the beads, in terms of probability, there are cases where the beads in which the template DNA could not be immobilized and when two different types of template DNA were replicated on one bead exist as defective beads. In these cases, the signals of the bases cannot be obtained, or, two types of signals are simultaneously obtained, and thus, cannot be used as data. There is another method regarding the method and the like for the adjustment of the concentration of the aqueous solution for decreasing the defective beads in which two types of template DNA were replicated, and selecting the beads in which the template DNA was immobilized beads and in which the template DNA was not immobilized, thus, the validity of the data obtained from the array spot can be improved. However, this is a well-known technology in emulsion PCR, and the presence or absence of the use of these technologies is not specifically limited in the present embodiment.

The present embodiment shows an example in which the template DNA was amplified in advance on the surface of the beads by emulsion PCR, and the template DNA immobilized on the array spot on which the beads were surface-modified by an amino group was analyzed by fluorescence measurement. However, it is also possible to use a kit of the beads with the resin substrate in the analysis of the beads which amplified the template DNA on the surface by emulsion PCR. For example, the resin substrate (without the loading of the functional group surface-modified beads, for example, the form arranged in the flow cell) in which the bead sitting positions of the two-dimensional array are set due to the uneven pattern formed on the surface, and the kit of the oligo DNA surface-modified beads (for example, the liquid in which the beads are dispersed) are separately supplied to the user, the oligo DNA surface-modified beads of the kit are used to amplify the template DNA which is the object for analysis on the beads in advance by emulsion PCR. Without supplying the template DNA beads containing the reagent 703 to the flow cell, a centrifugal force and the like is utilized to form the spot array substance by fitting into the bead sitting positions of the substrate, and this may be used to perform the analyses. In this case, it is also necessary for the user to perform the loading step of the beads himself/herself, but the base member itself is produced at a low cost, thus, the advantage that the user can perform a low cost analysis does not change.

Fifth Embodiment

The Fifth Embodiment illustrates another example of the analysis which uses the flow cell which incorporates the spot array substrate.

Figure 17:
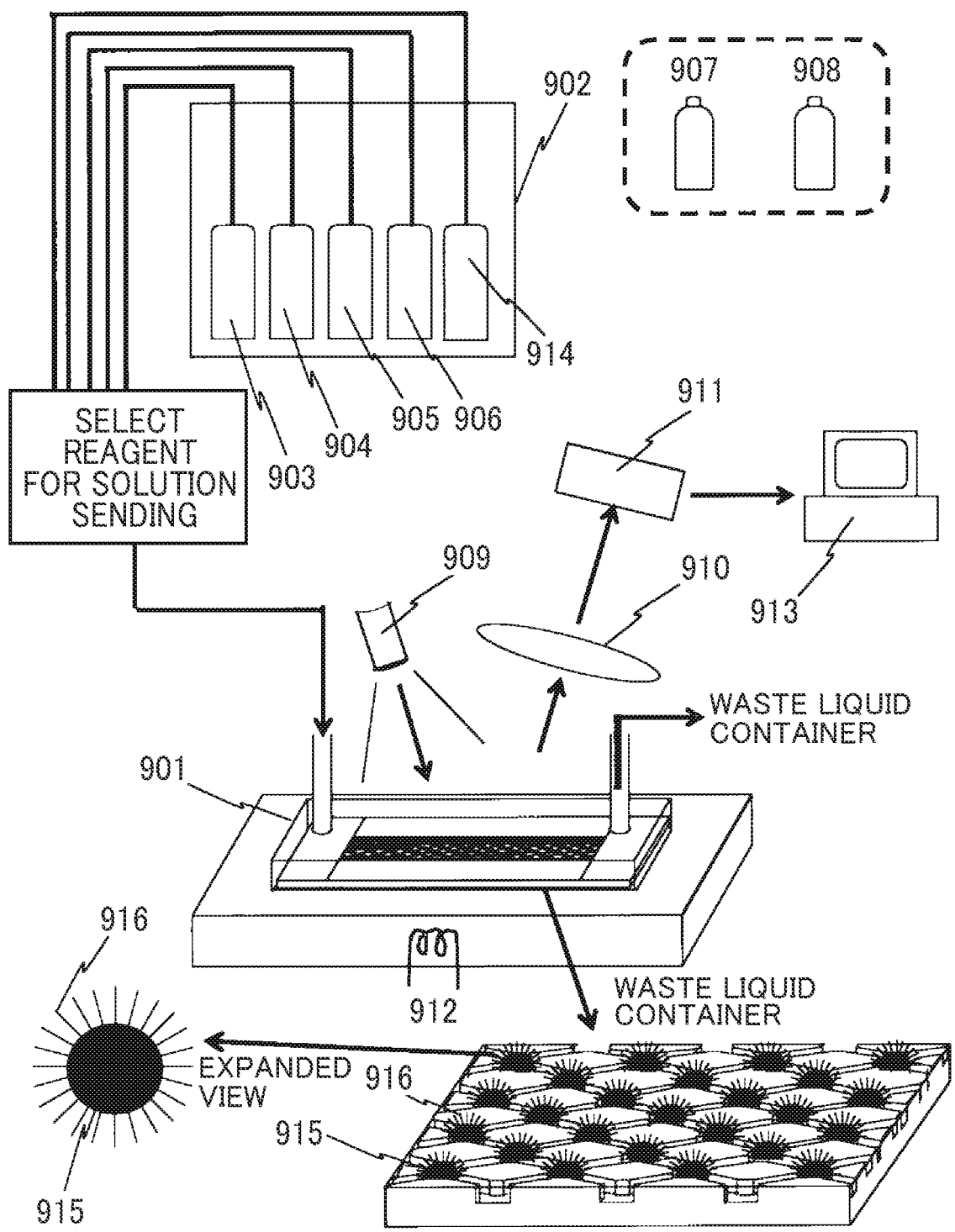
FIG. 17 is a schematic drawing illustrating a configuration example of the nucleic acid polymer analysis device.

FIG. 17 is a schematic drawing illustrating a configuration example of the nucleic acid polymer analysis device used in the present embodiment. A spot array substrate made of resin is incorporated in a flow cell 901. The solution introduced through the solution inlet of the flow cell 901 soaks the surface of the spot array substrate, and is discharged from the solution outlet to a waste liquid container. The bead sitting positions of the cycloolefin substrate in which the uneven pattern was formed by the convex portion of the densely arranged rhombuses and the shape of the groove surrounding the convex portion are used as the spot array substrate, namely, a substrate in which oligo DNA surface-modified beads 915 were fitted by the centrifugal force in the intersection point position of the groove surrounding the rhombic pattern was used. The basic material of the beads is silica. Further, the beads use a silica in which the particle size distribution was CV3%, and the filling rate of the beads into the bead sitting positions of the spot array substrate was 95%. The template DNA having an unknown sequence in at least the portion which was the object for analysis was immobilized on the array spot surface-modified with an oligo DNA, and then, replicated on the spot, the replica of the template DNA was analyzed by fluorescence measurement, and the base sequence was decoded.

As stated in the first to fourth embodiments, it is possible that the resin substrate in which the bead sitting positions of the two-dimensional array were set with the uneven pattern formed on the surface and the beads surface-modified with an oligo DNA are supplied separately to the user, and the user fits the beads in the bead sitting positions of the substrate to form the functional group spot array substrate and uses this substrate.

The temperature control of the flow cell 901 is possible by a temperature adjusting function 912. Further, a reaction reagent unit 902 for supplying several reaction reagents is installed and held at a low temperature where the enzyme reaction does not progress within the reagent, and is connected to the flow cell 901 with piping tubes. In the present embodiment, five types of reagents 903 to 906 and 914 can be supplied by the reaction reagent unit 902. The reagent 903 contains the material (template DNA 916 bound with complementary sequence) which binds the template DNA having an unknown sequence in at least the portion which is the object for analysis to the oligo DNA (known sequence) on the array spot to the complementary sequence. The reagent 914 includes dATP, dGTP, dCTP, dTTP, and an enzyme, and is a reagent for replicating on the array spot. The reagent 904 includes dATP-fluorescent dye 1, dGTP-fluorescent dye 2, dCTP-fluorescent dye 3, dTTP-fluorescent dye 4, a primer of a sequence complementary with the oligo DNA (known sequence) on the array spot, and the elongation reaction enzyme. The reagent 905 is a dye bond cleaving reagent for cleaving the bond between the four types of dNTP and the fluorescent dye. The reagent 906 is an electrolyte solution. Further, in the same manner as the fourth embodiment, isopropyl alcohol 907 and an electrolyte solution 908 which is the equivalent of the reagent 906 were separately prepared. Isopropyl alcohol 907 is used in the solution replacement within the flow cell 901, and another alcohol such as ethyl alcohol may be used.

A light source 909 for exciting each type of fluorescent dye contained in the reagent 904, an optical system 910 for measuring the fluorescence from the various dyes, and a photodetector array 911 are arranged above the flow cell 901. The optical signals received by the photodetector array 911 are converted to electric signals to be transferred to the analyzing device 913 for analyzing the fluorescence. The analyzing device 913 performs analyses such as the discrimination of the bases from the transferred signals and the connecting of fragment data, and decodes the base sequence of the nucleic acid polymer. Note that, in the same manner as the fourth embodiment, various selections of the fluorescent dyes 1 to 4 are contained in the reagent 904, and thus, can be used to select a suitable dye. Further, a suitable wavelength from the light source 909 for efficiently exciting these fluorescent dyes can be selected by the selection of these dyes.

First, isopropyl alcohol 907 was injected through the inlet of the flow cell 901 by a manual operation using a pipette and after verifying that there were no air bubbles, the isopropyl alcohol 907 was replaced with the electrolyte solution 908 by a manual operation using a pipette. Next, the flow cell 901 was set in the nucleic acid polymer analysis device with the electrolyte solution 908 filled in the cell and the air bubbles removed.

Next, the reagent 903 containing the template DNA 916 bound with complementary sequence was automatically injected into the flow cell 901 by a solution sending unit, the solution sending was stopped once in this state, the reagent 903 was set to the optimal temperature, left standing for 10 minutes, and immobilized on the oligo DNA-modified spot array. Since the material of the substrate was hydrophobic, no evidence that the template DNA 916 bound with complementary sequence was adsorbed other than in the spot array was observed, and the nonspecific adsorption was not a problem. Then, a suitable temperature was set, the reagent 914 for replicating on the array spot was supplied to the flow cell, the solution sending was stopped once in this state, the optimal temperature was set to repeat the elongation reaction and the denaturing, and the template DNA was replicated on the array spot. 95% of the oligo DNA-modified spot array material (oligo DNA surface-modified beads 915) during production was embedded in the cycloolefin substrate incorporated into the flow cell 901. Among them, the template DNA 916 bound with complementary sequence could be immobilized in a certain proportion of spots determined by probability theory. In this case, the concentration of the template DNA within the reagent 903 is different. Then, a suitable temperature was set, the reagent 904 was supplied to the flow cell, hybridized with a primer, and the elongation reaction was conducted with an enzyme. At this time, since the dNTP within the reagent was terminated by the fluorescent dye, after conducting the elongation reaction on the first base type of the template DNA, the reaction was stopped. Then, the excitation light was illuminated by the light source 909, and at this time, the emitted fluorescence was measured by the optical system 910 and the photodetector array 911.

Figure 18:
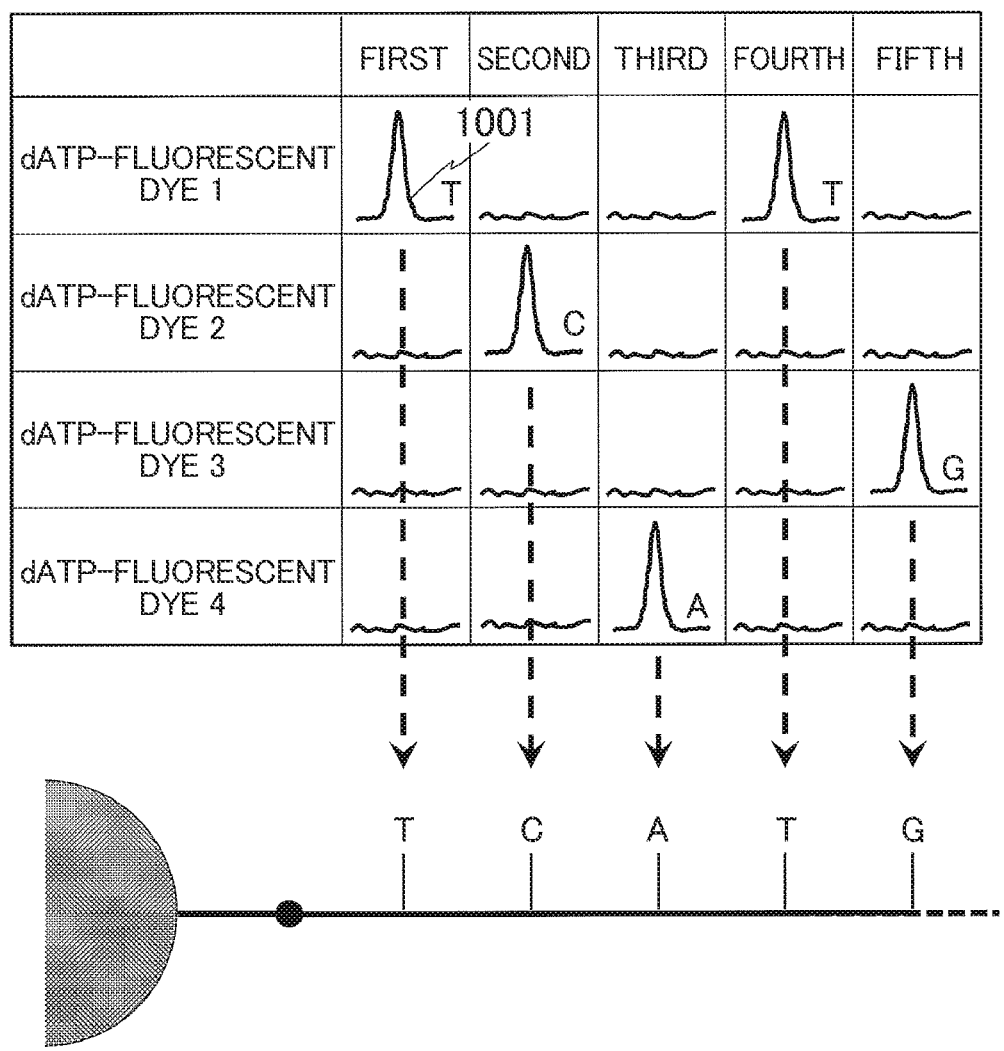
FIG. 18 is a graph illustrating an example of the measurement result of the fluorescence.

FIG. 18 illustrates an example of the measurement result of the fluorescence emitted by exciting with the light source 909 after conducting an elongation reaction in one of the array spots on the cycloolefin substrate incorporated in the flow cell 901. Since the fluorescence of the fluorescent dye 1 bound to dATP was verified in the first data 1001, the first base was decoded as T. Then, the dye was cleaved at a suitable temperature by the reagent 905 including the dye bond cleaving reagent for cleaving the bond between the four types of dNTP and the fluorescent dyes, and after washing the liquid within the flow cell containing the cleaved dye with the electrolyte solution of the reagent 906, the reagent 904 was automatically injected again, and the second or subsequent analysis of the bases was repeated in the same manner. As shown in FIG. 18, the measurement was performed until the fifth time (until the fifth base), and as a result, the alignment of the bases until the fifth base from the connection terminal of the oligo DNA on the oligo DNA-modified beads one of the selected array spots could be decoded as TCATG.

Note that, in the present embodiment, it is necessary that the replica of the template DNA immobilized on the one array spot which was modified by the oligo DNA is the replica of one type of template DNA. In the replica on the array spot which was modified by the oligo DNA, with the exception that the template DNA replicated on one spot is one type, in terms of probability, there are cases where the spot in which the template DNA could not be immobilized and where two different types of template DNA were replicated on one spot exist as defective beads. In these cases, the signals of the bases cannot be obtained, or, two types of signals are simultaneously obtained, and thus, cannot be used as data. Another method regarding the method and the like for the adjustment of the concentration of the aqueous solution for decreasing the defective spots in which two types of template DNA were replicated and for immobilizing the template DNA to the spot in which the template DNA could not be immobilized has been proposed, and thus, the validity of the data obtained from the array spot can be improved. For example, the method described in US 2012/0156728 A1, etc., can be used as the protocol for the replica on the substrate of the template DNA. The present embodiment is not limited to, specifically, the details of the replica technology on these substrates, and the details of the protocol are not specifically shown.

Note that, in the fourth and fifth embodiments, the flow cell which incorporated the spot array substrate by the present invention is used to perform the replica on the beads by emulsion PCR and the replica on the array spot of the substrate, and decode the DNA containing the partially unknown base sequence which is the object for analysis, but it goes without saying that the flow cell which incorporates the spot array substrate of the present invention can be used in the decoding not only DNA but also other nucleic acid polymers such as RNA.

Further, in the drawings corresponding to the explanation of the present invention, a mark of a heat filament and a mark of a convex lens are used symbolically in the temperature adjusting function and the optical system. However, the temperature adjusting function also includes functions for cooling such as air cooling, water cooling, and a cooling element, and can be controlled to a fixed temperature by a general temperature control method such as PID control, and the optical system has a light separating function such as a spectrometer and a color filter other than a convex lens, thus, it goes without saying that the color of the fluorescence can be distinguished.

Note that, the present invention is not limited to the above-described embodiments but includes various modifications. The above-described embodiments are explained in detail for better understanding of this invention and are not limited to those including all the configurations described above. A part of the configuration of one embodiment may be replaced with that of another embodiment; and the configuration of one embodiment may be incorporated to the configuration of another embodiment. A part of the configuration of each embodiment may be added, deleted, or replaced by that of a different configuration.

LIST OF REFERENCE SIGNS 204 resin substrate
207 centrifuge
208 amino group surface-modified magnetic beads
210 magnet
304 convex portion
305 mold
306 resin substrate
405 centrifuge
701 flow cell
702 reaction reagent unit
709 light source
710 optical system
711 photodetector array
712 temperature adjusting function
713 analyzing device
714 amino group surface-modified beads
715 beads which formed replica of template DNA on surface
915 oligo DNA surface-modified beads
916 template DNA bound with complementary sequence

The invention claimed is:

1. A spot array substrate comprising:
   a resin substrate having a surface including an uneven pattern that includes a plurality of grooves that form rhombic patterns, and a plurality of bead sitting positions set in a two-dimensional array within the uneven pattern; and
   a plurality of surface-modified beads loaded into the bead sitting positions of the resin substrate,
   wherein a thermal expansion coefficient of a material of the resin substrate is in a range from $10^{-5}$ to $10^{-4}$/° C.,
   wherein the plurality of bead sitting positions are intersections of the plurality of grooves disposed in the resin substrate,
   wherein an epoxy group is disposed as a film only on inner surfaces of the respective plurality of grooves of the resin substrate,
   wherein the respective surface-modified beads loaded in the bead sitting positions are physically clamped by inner surfaces of the grooves of the bead sitting positions, which are physically contracted, and
   wherein the surface-modified beads are at least one of functional group surface-modified beads and oligo DNA surface-modified beads.

2. The spot array substrate according to claim 1, wherein the grooves have a smaller width than the dimensions of the bead sitting positions.

3. The spot array substrate according to claim 1, wherein the respective surface-modified beads are immobilized at the respective bead sitting positions of the resin substrate by chemical bonding.

4. The spot array substrate according to claim 1, wherein the bulk material of the surface-modified beads is a material including silicon oxide or a material including a magnetic body.

5. The spot array substrate according to claim 1, wherein the surface-modified beads are functional group surface-modified beads.

6. The spot array substrate according to claim 1, wherein the surface-modified beads are oligo DNA surface-modified beads.

7. The spot array substrate according to claim 1, wherein the resin substrate contains a cycloolefin polymer or a cycloolefin copolymer as a component.

8. The spot array substrate according to claim 1, wherein the surface density of the bead sitting positions is $6.6 \times 10^6$/cm$^2$ to $180 \times 10^6$/cm$^2$.

9. The spot array substrate according to claim 1, wherein a size of the respective surface-modified beads is equal to a size of the respective intersections of the grooves.

* * * * *